(12) United States Patent
Stoddart et al.

(10) Patent No.: US 11,977,028 B2
(45) Date of Patent: May 7, 2024

(54) MECHANICAL-BOND-INDUCED EXCIPLEX FLUORESCENCE

(71) Applicants: Northwestern University, Evanston, IL (US); KING ABDULAZIZ CITY FOR SCIENCE AND TECHNOLOGY (KACST), Riyadh (SA)

(72) Inventors: James Fraser Stoddart, Evanston, IL (US); Amine Garci, Evanston, IL (US); Yassine Beldjoudi, Wheeling, IL (US)

(73) Assignees: Northwestern University, Evanston, IL (US); King Abdulaziz City for Science and Technology (KACST), Riyadh (SA)

( * ) Notice: Subject to any disclaimer, the term of this patent is extended or adjusted under 35 U.S.C. 154(b) by 314 days.

(21) Appl. No.: 17/301,823

(22) Filed: Apr. 15, 2021

(65) Prior Publication Data
US 2021/0325310 A1   Oct. 21, 2021

Related U.S. Application Data

(60) Provisional application No. 63/010,249, filed on Apr. 15, 2020.

(51) Int. Cl.
*G01N 21/64* (2006.01)

(52) U.S. Cl.
CPC ..... *G01N 21/6486* (2013.01); *G01N 21/6408* (2013.01); *G01N 21/6428* (2013.01)

(58) Field of Classification Search
None
See application file for complete search history.

(56) References Cited

U.S. PATENT DOCUMENTS

| | | | | |
|---|---|---|---|---|
| 8,547,533 | B2* | 10/2013 | Knutson | C09B 23/086 436/139 |
| 10,889,554 | B2* | 1/2021 | Gunning | C09B 57/00 |
| 11,566,014 | B2* | 1/2023 | Nguyen | H10K 85/654 |
| 2004/0038306 | A1* | 2/2004 | Agnew | G01N 33/50 435/7.1 |
| 2011/0086420 | A1* | 4/2011 | Fischer | B01L 3/545 525/326.1 |

(Continued)

OTHER PUBLICATIONS

Lekha, P. K.; et al., Aggregation-Controlled Excimer Emission from Anthracene-Containing Polyamidoamine Dendrimers. Chem. Eur. J. 2010, 16, 3699-3706.

(Continued)

*Primary Examiner* — David P Porta
*Assistant Examiner* — Djura Malevic
(74) *Attorney, Agent, or Firm* — Quarles & Brady LLP

(57) ABSTRACT

Disclosed herein are methods for live-cell imaging, compositions for performing the live cell imaging, and methods for making the composition. The method may comprise contacting a cell with an effective amount of a catenane, irradiating the cell, and detecting exciplex emission from the catenane within the cell. The catenane may comprise two mechanically interlocked macrocycles, each of the two macrocycles comprise an aromatic fluorophore subunit, and the aromatic fluorophores are arranged in a face-to-face [π . . . π] stack allowing for the exciplex emission.

11 Claims, 16 Drawing Sheets

(56) References Cited

U.S. PATENT DOCUMENTS

| | | | | |
|---|---|---|---|---|
| 2012/0186639 | A1* | 7/2012 | Zang | B82Y 10/00 |
| | | | | 257/E51.026 |
| 2012/0296085 | A1* | 11/2012 | Smith | C07D 249/04 |
| | | | | 204/157.82 |
| 2012/0309045 | A1* | 12/2012 | Knutson | C09B 11/24 |
| | | | | 204/157.68 |
| 2016/0290998 | A1* | 10/2016 | Leif | G01N 21/6428 |
| 2017/0194585 | A1* | 7/2017 | Yan | H10K 85/611 |
| 2021/0147384 | A1* | 5/2021 | Nguyen | H10K 85/654 |
| 2021/0325310 | A1* | 10/2021 | Stoddart | G01N 21/6486 |
| 2023/0322781 | A1* | 10/2023 | Wu | C07D 471/22 |
| | | | | 252/301.16 |

OTHER PUBLICATIONS

Iu, H.; et al., Excimer-Induced High-Efficiency Fluorescence due to Pairwise Anthracene Stacking in a Crystal with Long Lifetime. Chem. Comm. 2016, 52, 7356-7359.

Liu, H.-W.; et al., An Efficient Two-photon Fluorescent Probe for Monitoring Mitochondrial Singlet Oxygen in Tissues During Photodynamic Therapy. Chem. Comm. 2016, 52, 12330-12333.

Liu, J.; et al., Pyridyl-Substituted Anthracene Derivatives with Solid-State Emission and Charge Transport Properties. J. Mater. Chem. C, 2016, 4, 3621-3627.

Lohani, C. R.; et al., Facile Synthesis of Anthracene-Appended Amino Acids as Highly Selective and Sensitive Fluorescent Fe3+ Ion Sensors. Bioorg. Med. Chem. Lett. 2009, 19, 6069-6073.

Luo, J.; et al., pi-Conjugated oligothiophene-anthracene co-oligomers: synthesis, physical properties, and self-assembly. J. Mater. Chem. 2009, 19, 8202-8211.

Mcvey, J. K.; et al., Direct Observation and Characterization of Anthracene Excimer in Solution. Chem. Phys. 1976, 65, 3375-3376.

Mehta, G.; et al., Triquinane-Derived Macrocyclic Lactones and a [2]-Catenane: Synthesis and Characterization. Tetrahedron 1998, 54, 10879-10890.

Mitra, R.; et al., A Bifunctional Chiral [2]Catenane Based on 1,1'-Binaphthyl-Phosphates. Chem. Comm. 2016, 52, 5977-5980.

Musser, A. J.; et al., Intermolecular States in Organic Dye Dispersions: Excimers vs. Aggregates. J. Mater. Chem. 2017, 5, 8380-8389.

Nandajan, P. C.; et al., Interplay of Monomer, Intra- and Intermolecular Excimer Fluorescence in Cyclophanes and Selective Recognition of Methanol Vapours. RSC Adv. 2013, 3, 5624-5630.

Nangia, A., Conformational Polymorphism in Organic Crystals. Acc. Chem. Res. 2008, 41, 595-604.

Neal, E. A.; et al., Chemical Consequences of Mechanical Bonding in Catenanes and Rotaxanes: Isomerism, Modification, Catalysis and Molecular Machines for Synthesis. Chem. Comm. 2014, 50, 5128-5142.

Ojida, A.; et al., First Artificial Receptors and Chemosensors Toward Phosphorylated Peptide in Aqueous Solution. J. Am. Chem. Soc. 2002, 124, 6256-6258.

Osaki, H.; et al., A Macrocyclic Fluorophore Dimer with Flexible Linkers: Bright Excimer Emission with a Long Fluorescence Lifetime. Angew. Chem. 2016, 55, 7131-7135.

Ronson, T. K.; et al., Design Principles for the Optimization of Guest Binding in Aromatic-Paneled FeII4L6 Cages. J. Am. Chem. Soc. 2017, 139, 9698-9707.

Roy, I.; et al., A Supramolecular Approach for Modulated Photoprotection, Lysosomal Delivery, and Photodynamic Activity of a Photosensitizer. J. Am. Chem. Soc. 2019, 141, 12296-12304.

Roy, I.; et al., ExTzBox: A Glowing Cyclophane for Live-Cell Imaging. J. Am. Chem. Soc. 2018, 140, 7206-7212.

Ryan, S. T. J.; et al., Energy and Electron Transfer Dynamics within a Series of Perylene Diimide/Cyclophane Systems. J. Am. Chem. Soc. 2015, 137, 15299-15307.

Sagara, Y.; et al., Rotaxane-Based Mechanophores Enable Polymers with Mechanically Switchable White Photoluminescence. ACS Cent. Sci. 2019, 5, 874-881.

Sagara, Y.; et al., Rotaxanes as Mechanochromic Fluorescent Force Transducers in Polymers. J. Am. Chem. Soc. 2018, 140, 1584-1587.

Santiago-Gonzalez, B.; et al., Permanent Excimer Superstructures by Supramolecular Networking of Metal Quantum Clusters. Science 2016, 353, 571-575.

Sauvage, J.-P., From Chemical Topology to Molecular Machines (Nobel Lecture). Angew. Chem. Int. Ed. 2017, 56, 11080-11093.

Seo, B. M.; et al., Efficient Orange-Red Organic Light-Emitting Diodes using 9,10-bis[4-(di-4-tert-butylphenylamino) styryl] Anthracene as a Fluorescent Orange-Red Emitter. Thin Solid Films. 2010, 518, 6214-6218.

Shen, Y.; et al., Discrete Face-to-Face Stacking of Anthracene Inducing High-Efficiency Excimer Fluorescence in Solids via a Thermally Activated Phase Transition. J. Mater. Chem. C 2017, 5, 10061-10067.

Song, J. Y.; et al., Novel Fluorescent Blue-Emitting Materials Based on Anthracene-Fluorene Hybrids with Triphenylsilane Group for Organic Light-Emitting Diodes. Dyes Pigm. 2015, 114, 40-46.

Stoddart, J. F., Mechanically Interlocked Molecules (MIMs)- Molecular Shuttles, Switches, and Machines (Nobel Lecture). Angew. Chem. Int. Ed. 2017, 56, 11094-11125.

Stoddart, J. F., The Chemistry of the Mechanical Bond. Chem. Soc. Rev. 2009, 38, 1802-1820.

Sugino, M.; et al., Elucidation of Anthracene Arrangement for Excimer Emission at Ambient Conditions. Cryst. Growth Des. 2013, 13, 4986-4992.

Sun, B.; et al., Design and Application of Anthracene Derivative with Aggregation-Induced Emission Charateristics for Visualization and Monitoring of Erythropoietin Unfolding. Langmuir 2013, 29, 1956-1962.

Sun, J.; et al., Mechanical-Bond-Protected, Air-Stable Radicals. J. Am. Chem. Soc. 2017, 139, 12704-12709.

Theil, A.; et al., Phosphorus-Containing [2]Catenanes as an Example of Interlocking Chiral Structures. Angew. Chem. Int. Ed. 2006, 45, 2104-2107.

Thordarson, P. Determining Association Constants from Titration Experiments in Supramolecular Chemistry. Chem. Soc. Rev., 2011, 40, 1305-1323.

Trabolsi, A.; et al., Radically Enhanced Molecular Recognition. Nat. Chem. 2010, 2, 42-49.

Uttam, B .; et al., Proficient Molecular Receptor Exhibiting "On-Off" Excimer Fluorescence with Fluoride and Mercury Toxicants. J. Photochem. Photobiol. 2017, 349, 224-229.

Vasylevskyi, S. I.; et al., Anion-Induced Structural Diversity of Zn and Cd Coordination Polymers Based on Bis-9,10-(pyridine-4-yl)-anthracene, Their Luminescent Properties, and Highly Efficient Sensing of Nitro Derivatives and Herbicides. Inorg. Chem. 2019, 58, 5646-5653.

Vögtle, F.; et al., One-Step Synthesis of a Fourfold Functionalized Catenane. Angew. Chem. Int. Ed. 1992, 31, 1619-1622.

Vollbrecht, J., Excimers in Organic Electronics. New J. Chem. 2018, 42, 11249-11254.

Wang, C.; et al., Cruciforms: Assembling Single Crystal Micro- and Nanostructures from One to Three Dimensions and their Applications in Organic Field-Effect Transistors. Chem. Mater. 2009, 21, 2840-2845.

Wang, C.-Y.; et al., Precursor Control Over the Self-Assembly of [2]Catenanes via Hydrazone Condensation in Water. Chem. Comm. 2018, 54, 5106-5109.

Wang, W.; et al., Cyclization and Catenation Directed by Molecular Self-Assembly. J. Am. Chem. Soc. 2006, 128, 11150-11159.

Wang, Y.; et al., Introducing Stable Radicals into Molecular Machines. ACS Cent. Sci. 2017, 3, 927-935.

Wu, G.; et al., Controllable Self-Assembly of Macrocycles in Water for Isolating Aromatic Hydrocarbon Isomers. J. Am. Chem. Soc. 2018, 140, 5955-5961.

Wu, Y.; et al. Probing Distance Dependent Charge-Transfer Character in Excimers of Extended Viologen Cyclophanes Using Femtosecond Vibrational Spectroscopy. J. Am. Chem. Soc. 2017, 139, 14265-14276.

Yoshizawa, M.; et al., Bent Anthracene Dimers as Versatile Building Blocks for Supramolecular Capsules. Acc. Chem. Res. 2019, 52, 2392-2404.

(56) References Cited

OTHER PUBLICATIONS

Yoshizawa, M.; et al., Molecular Architectures of Multi-Anthracene Assemblies. Chem. Soc. Rev. 2014, 43, 1885-1898.
Zhang, G.; et al., A Highly Fluorescent Anthracene-Containing Hybrid Material Exhibiting Tunable Blue-Green Emission Based on the Formation of an Unusual "T-Shaped" Excimer. Chem. Eur. J. 2007, 13, 3630-3635.
Zhao, C.; et al., Excimer Formation from Particially Overlapped Anthracene Dimer Based on Saddle-Shaped Cyclooctatetrathiophene as Spacer. J. Photochem. Photobiol. 2018, 355, 318-325.
Amicangelo, J. C. et al. Excimer Formation in the Interlayer Region of Arene-Derivatized Zirconium Phosphonates. J. Am. Chem. Soc. 2003, 125, 14698-14699.
Au-Yeung, H. Y.; et al., Strategies to Assemble Catenanes with Multiple Interlocked Macrocycles. Inorg. Chem. 2018, 57, 3475-3485.
Baba, M.; et al., Structure and Excited-State Dynamics of Anthracene: Ultrahigh-Resolution Spectroscopy and Theoretical Calculation. J. Chem. Phys. 2009, 130, 134315-134325.
Babu, S. S.; et al., Nonvolatile Liquid Anthracenes for Facile Full-Colour Luminescence Tuning at Single Blue-Light Excitation. Nat. Commun. 2013, 4, 1969.
Banerjee, S.; et al., Probing the Aggregation and Signaling Behavior of Some Twisted 9,9'-Bianthryl Derivatives: Observation of Aggregation-Induced Blue-Shifted Emission. ACS Omega 2018, 3, 15709-15724.
Barin, G.; et al., Mechanically Interlocked Molecules Assembled by pi-pi Recognition. ChemPlusChem. 2012, 77, 159-185.
Barnes, J. C.; et al., A Radically Configurable Six-State Compound. Science 2013, 339, 429-433.
Barnes, J. C.; et al., ExBox: A Polycyclic Aromatic Hydrocarbon Scavenger. J. Am. Chem. Soc. 2013, 135, 183-192.
Barnes, J. C.; et al., Solid-State Characterization and Photoinduced Intramolecular Electron Transfer in a Nanoconfined Octacationic Homo[2]Catenane. J. Am. Chem. Soc. 2014, 136, 10569-10572.
Barnes, R. L.; et al., 'Excimer' Fluorescence—X. Spectral Studies of 9-Methyl and 9, 10-Dimethyl Anthracene. Proc. R. Soc. Lond. 1966, 291, 570-582.
Beldjoudi, Y.; et al., Structural, Magnetic, and Optical Studies of the Polymorphic 9'-Anthracenyl Dithiadiazolyl Radical. J. Am. Chem. Soc. 2019, 141, 6875-6889.
Birks, J. B.; et al., Excimer Formation in Polycyclic Hydrocarbons and their Derivatives. Nature 1963, 197, 1064-1065.
Bouas-Laurent, H.; et al., Photodimerization of Anthracenes in Fluid Solution: Structural Aspects. Chem. Soc. Rev. 2000, 29, 43-55.
Bouas-Laurent, H.; et al., Photodimerization of anthracenes in Fluid Solutions: (Part 2) Mechanistic Aspects of the Photocycloaddition and of The Photochemical and Thermal Cleavage. Chem. Soc. Rev. 2001, 30, 248-263.
Bruns, C. J.; et al., Emergent Ion-Gated Binding of Cationic Host-Guest Complexes Within Cationic M12L24 Molecular Flasks. J. Am. Chem. Soc. 2014, 136, 12027-12034.
Caballero, A.; et al., A Halogen-Bonding Catenane for Anion Recognition and Sensing. Angew. Chem. Int. Ed. 2012, 51, 1876-1880.
Chae, M. K.; et al., A Catenated Anion Receptor Based on Indolocarbazole. Tetrahedron Lett. 2010, 51, 4240-4242.
Chan, J.; et al., Reaction-Based Small-Molecule Fluorescent Probes for Chemoselective Bioimaging. Nat. Chem. 2012, 4, 973-984.
Chen, J.; et al., Excimer Formation in Crystalline and Nanostructured Coordination Polymers. Chem. Comm. 2010, 46, 8282-8284.
Chen, K.-H.; et al., Phospholipid-Induced Aggregation and Anthracene Excimer Formation. Org. Lett. 2008, 10, 4401-4404.
Chen, X.-M.; et al., Supramolecular Assemblies with Near-Infrared Emission Mediated in Two Stages by Cucurbituril and Amphiphilic Calixarene for Lysosome-Targeted Cell Imaging. Angew. Chem. Int. Ed. 2018, 57, 12519-12523.
Chen, Z.; et al., Self-Assembled pi-Stacks of Functional Dyes in Solution: Structural and Thermodynamic Features. Chem. Soc. Rev. 2009, 38, 564-584.
David, A. H. G.; et al., A [2]Rotaxane-Based Circularly Polarized Luminescence Switch. J. Am. Chem. Soc. 2019, 141, 18064-18074.
Daze, K. et al. (2016). Molecular Interaction and Recognition. In Encyclopedia of Physical Organic Chemistry (eds Z. Wang, U. Wille and E. Juaristi). doi:10.1002/9781118468586.epoc3001.
Dietrich-Buchecker, C. O.; et al., Templated Synthesis of Interlocked Macrocyclic Ligands: The Catenands. J. Am. Chem. Soc. 1984, 106, 3043-3045.
Dimitriev, O. P.; et al., Abnormal Emission in the Heterogeneous J-Aggregate System. J. Phys. Chem. C. 2019, 123, 28611-28619.
Erdemir, S.; et al., Anthracene Excimer-Based "Turn On" Fluorescent Sensor for Cr3+ and Fe3+ Ions: Its Application to Living Cells. Talanta 2016, 158, 63-69.
Evans, N. H.; et al., Progress in the Synthesis and Exploitation of Catenanes Since the Millennium. Chem. Soc. Rev. 2014, 43, 4658-4683.
Fleetham, T.; et al., Efficient and Stable Single-Doped White OLEDs Using a Palladium-Based Phosphorescent Excimer. Chem. Sci. 2017, 8, 7983-7990.
Fudickar, W.; et al., Synthesis of Pyridylanthracenes and their Reversible Reaction with Singlet Oxygen to Endoperoxides. J. Org. Chem., 2017, 82, 9258-9262.
Fujita, M.; et al., Quantitative Self-Assembly of a [2]Catenane from Two Preformed Molecular Rings. Nature 1994, 367, 720-723.
Gaigalas, A. K.; et al., The Development of Fluorescence Intensity Standards. J. Res. Natl. Inst. Stand. Technol. 2001, 106, 381-389.
Gao, Y.; et al., Excimer Formation and Evolution of Excited State Properties in Discrete Dimeric Stacking of an Anthracene Derivative: A Computational Investigation. Phys. Chem. Chem. Phys. 2018, 20, 12129-12137.
Ghosh, K.; et al., An Anthracene Based Bispyridinium Amide Receptor for Selective Sensing of Anions. Tetrahedron Lett. 2007, 48, 8725-8729.
Gil-Ramírez, G.; et al., Catenanes: Fifty Years of Molecular Links. Angew. Chem. Int. Ed. 2015, 54, 6110-6150.
Gong, X.; et al., Toward a Charged Homo[2]catenane Employing Diazaperopyrenium Homophilic Recognition. J. Am. Chem. Soc. 2018, 140, 6540-6544.
Griffiths K., E.; et al., Template-Directed Synthesis of Donor/Acceptor [2]Catenanes and [2]Rotaxanes. Pure Appl. Chem. 2008, 80, 485-506.
Hayashi, K.; et al., Observation of Circularly Polarized Luminescence of the Excimer from Two Perylene Cores in the Form of [4]Rotaxane. Chem. Eur. J. 2018, 24, 14613-14616.
Hestand, N. J.; et al., Expanded Theory of H- and J-Molecular Aggregates: The Effects of Vibronic Coupling and Intermolecular Charge Transfer. Chem. Rev. 2018, 118, 7069-7163.
Hou, Y.; et al., Charge Separation, Charge Recombination, Long-Lived Charge Transfer State Formation and Intersystem Crossing in Organic Electron Donor/Acceptor Dyads. J. Mater. Chem. C 2019, 7, 12048-12074.
Hunter, C. A., Synthesis and Structure Elucidation of a New [2]-Catenane. J. Am. Chem. Soc. 1992, 114, 5303-5311.
Inouye, M.; et al., A Doubly Alkynylpyrene-Threaded [4]Rotaxane That Exhibits Strong Circularly Polarized uminescence from the Spatially Restricted Excimer. Angew. Chem. Int. Ed. 2014, 53, 14392-14396.
Johnston, A. G.; et al., Facile Synthesis and Solid-State Structure of a Benzylic Amide [2]Catenane. Angew. Chem. Int. Ed. 1995, 34, 1209-1212.
Johnston, A. G.; et al., Structurally Diverse and Dynamically Versatile Benzylic Amide [2]Catenanes Assembled Directly from Commercially Available Precursors. Angew. Chem. Int. Ed. 1995, 34, 1212-1216.
Juricek, M.; et al., An ExBox[2]Catenane. Chem. Sci. 2014, 5, 2724-2731.
Kaanumalle, L. S.; et al., A Hydrophobic Nanocapsule Controls the Photophysics of Aromatic Molecules by Suppressing Their Favored Solution Pathways. J. Am. Chem. Soc. 2005, 127, 3674-3675.

(56) References Cited

OTHER PUBLICATIONS

Kodaimati, M. S.; et al., Energy Transfer-Enhanced Photocatalytic Reduction of Protons within Quantum Dot Light-Harvesting-Catalyst Assemblies. Proc. Natl. Acad. Sci. USA 2018, 115, 8290-8295.

Kwon, O.-H.; et al., Formation Mechanism of Anthracene Dimers and Excimers in NaY Zeolitic Nanocavities. J. Phys. Chem. B. 2004, 108, 3970-3974.

Lee, K. H.; et al., Molecular Engineering of Blue Fluorescent Molecules Based on Silicon End-Capped Diphenylaminofluorene Derivatives for Efficient Organic Light-Emitting Materials. Adv. Funct. Mater. 2010, 20, 1345-1358.

Lehmann, M.; et al., At the Limits of Liquid Crystallinity: Stimuli Responsive 3D Columnar Liquid Crystals and Soft Crystals of Supramolecular Anthracene Mesogens. Chem. Mater. 2015, 27, 8181-8184.

* cited by examiner

SCHEME 1

FIG. 1B
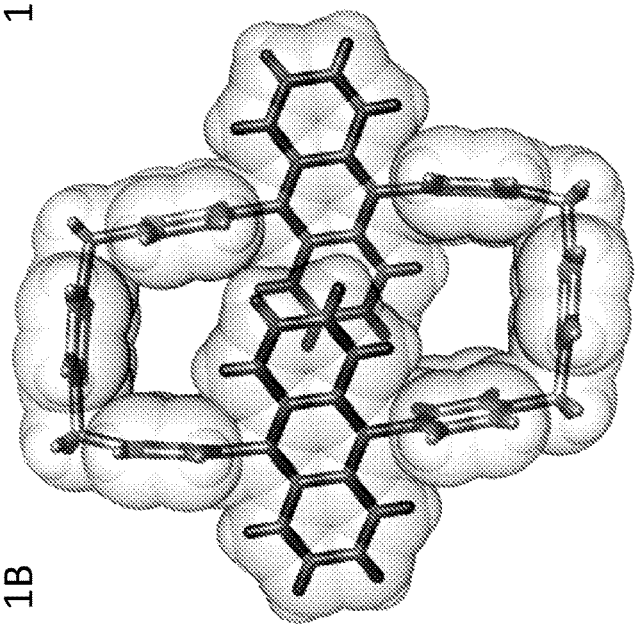
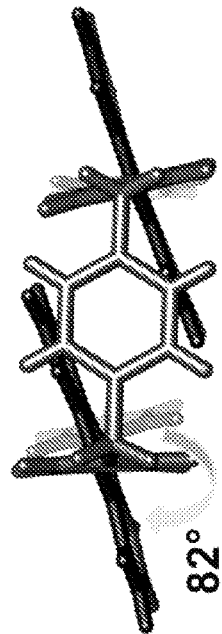
FIG. 1C
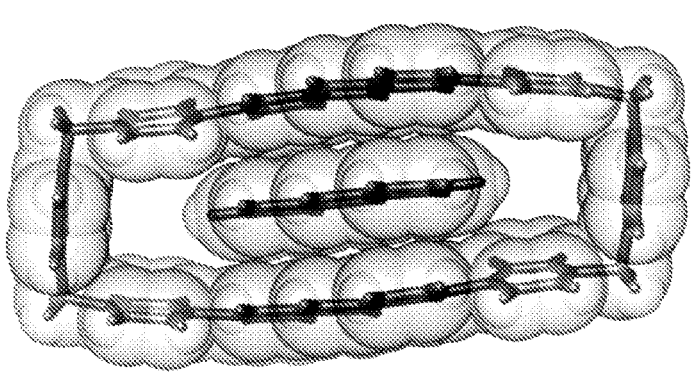
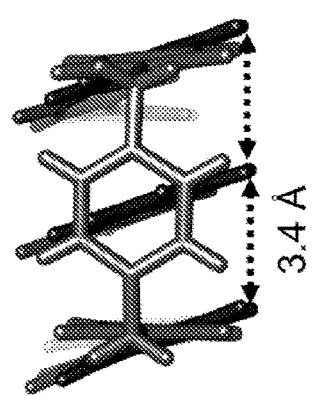
FIG. 1D
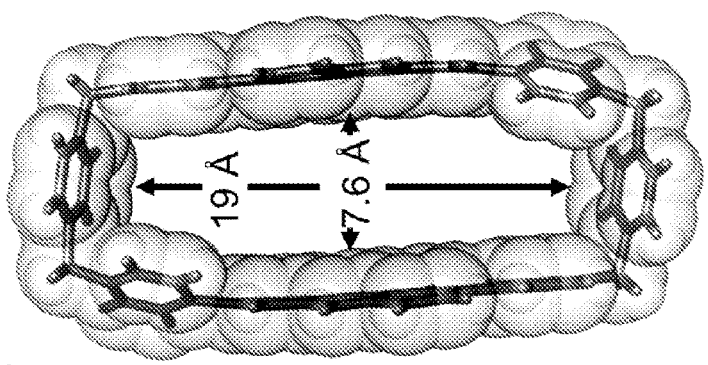
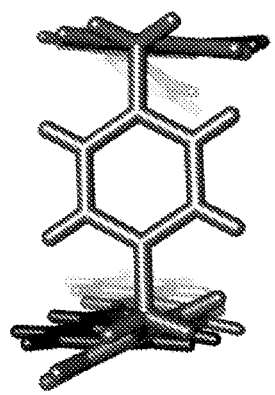

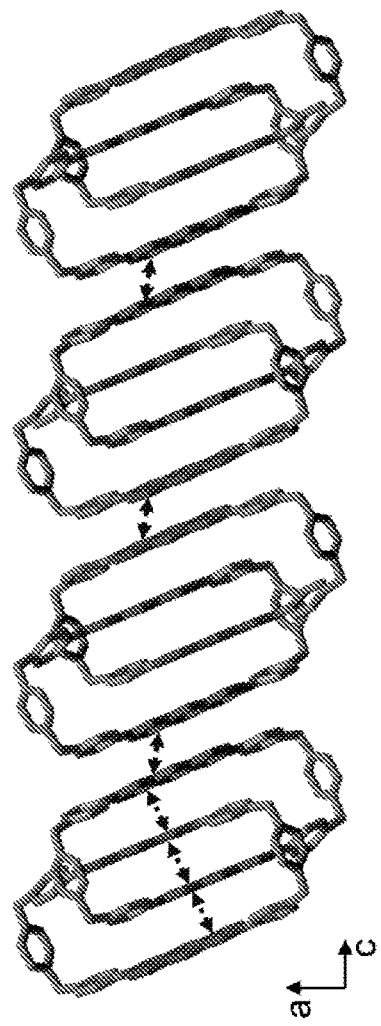
FIG. 3A α-Polymorph
FIG. 3B Regular π-stack 3.4 Å
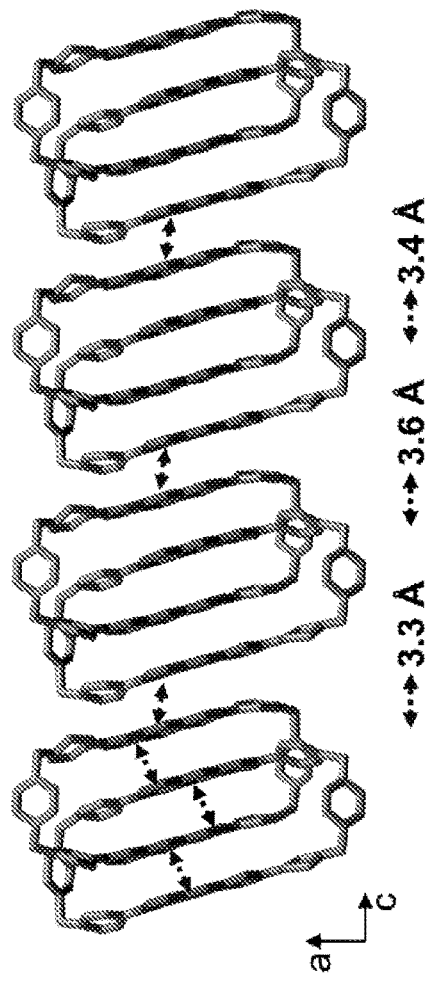
FIG. 3C β-Polymorph
FIG. 3D Irregular π-stack 3.4 Å 3.6 Å 3.3 Å

MECHANICAL-BOND-INDUCED EXCIPLEX FLUORESCENCE

CROSS-REFERENCE TO RELATED APPLICATIONS

This application claims benefit of priority to U.S. application Ser. No. 63/010,249 filed Apr. 15, 2020, the contents of which is incorporated by reference in its entirety.

BACKGROUND OF THE INVENTION

Collisional intermolecular interactions between excited states form short-lived dimers and complexes that lead to the emergence of excimer/exciplex emission of lower energy, a phenomenon which must be differentiated from the photoluminescence (PL) arising from the monomeric molecules. Although the utilization of noncovalent bonding interactions, leading to the generation of excimer/exciplex PL, has been investigated extensively, precise control of the aggregates and their persistence at very low concentrations remains a rare phenomenon.

Anthracene can be used as tools for bio-imaging,[1] molecular sensors,[2] and the construction of photo-emissive organic materials.[3] Compounds containing anthracene molecules are well known[1-4] to exhibit intense fluorescence in dilute solution, and several strategies have been proposed[4] to tune the wavelength of the emission and enhance its efficiency. Organic π-fluorophores, such as anthracene, show a strong tendency to form H- and J-type aggregates in highly concentrated solutions[5] as well as in crystalline[6] and liquid-crystalline[7] states. The photophysical properties resulting from close [π . . . π] stacking is often different from those observed when the chromophores exist as single units in dilute solutions[8] or in polymer matrices.[9] Excimer/exciplex emissions often display[10] bathochromic shifts associated with exciton delocalization among two or more molecules. Initially, excimers were considered[11] detrimental to fluorescence efficiency because their quantum yields are lower than those of the isolated molecules. Recently, interest has grown[12] in achieving efficient excimer/exciplex emissions because of their potential tuneability in the solid state and low-energy excitations and emissions. Li and coworkers[13] have reported an excimer-based white organic light-emitting diode (WOLED), which displays a broad white emission arising from both the monomer and the excimer. Gonzalez and coworkers[14] have developed a permanent gold superstructure, stabilized by a network of hydrogen bonds which showed efficient excimer emission in the red optical region at high dilutions. These nanoclusters were applied[13] as probes for live-cell imaging. Anthracene excimer photoluminescence (PL) has been reported in concentrated solutions,[15] aqueous media,[16] and in solid-state samples.[6] Excimer/exciplex photoluminescence (PL), nevertheless, presents several drawbacks associated with (i) anthracene excimer formation, which can be probed only at high concentrations[15,17] and, therefore, cannot be used in bio-imaging, for example, because of toxicity issues, (ii) PL quenching as the result of the photo-dimerization of anthracenes by [4+4] cycloaddition[18] and (iii) the difficulty of predicting the nature of the aggregates since the anthracene units can [π . . . π] interact[9,19] in either face-to-face or edge-to-face orientations. Several approaches for the generation of excimer/exciplex emissions have been reported,[20,22] by controlling the arrangement of the anthracene units in dendrimers,[20] in metal coordination complexes,[21] or through confinement within hosts.[22] The labile nature of these superstructures at high dilution, however, has prevented the observation of exciplex emissions. In this context, the design of new protocols for the construction of shape-persistent architectures with well-defined numbers of fluorophores and close intermolecular interactions is crucial for the generation of permanent exciplex PL at low concentrations for biomedical applications.

BRIEF SUMMARY OF THE INVENTION

Disclosed herein are catenanes and methods of using and making the same for live-cell imaging. One aspect of the invention is a method for live-cell imaging. The method may comprise contacting a cell with an effective amount of a catenane, irradiating the cell, and detecting exciplex emission from the catenane within the cell. The catenane may comprise two mechanically interlocked macrocycles, each of the two macrocycles comprise an aromatic fluorophore subunit, and the aromatic fluorophores are arranged in a face-to-face [π . . . π] stack allowing the formation of the exciplex emission. Suitably, the aromatic fluorophore may comprise an anthracene subunit.

Another aspect of the invention is crystalline compositions comprising a catenane for use in live-cell imaging. The crystalline composition may have a Monoclinic, C2/c molecular packing arrangement and lattice parameters a=41.8±0.1 Å, b=12.7±0.1 Å, c=29.0±0.1 Å, α=90.0±0.1°, β=94.5±0.1°, γ=90.0±0.1°. In another embodiment, the crystalline composition may have an Orthorhombic, P222$_1$ molecular packing arrangement and lattice parameters a=11.9±0.1 Å, b=14.2±0.1 Å, c=42.5±0.1 Å, α=90.0±0.1°, β=90.0±0.1°, γ=90.0±0.1°.

Another aspect of the invention is a method for preparing a catenane for use in live-cell imaging. The method may comprise preparing a first macrocycle comprising an aromatic fluorophore subunit in the presence of an aromatic template and mechanically interlocking the first macrocycle with a second macrocycle comprising a second aromatic fluorophore subunit in the presence of a salt. The mechanically interlocking the first macrocycle with the second macrocycle gives rise to the formation of the catenane in which the aromatic fluorophores are arranged in a face-to-face [π . . . π] stack allowing the generation of the exciplex emission.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 1B-1D show space-filling representations of the solid-state structures of (FIG. 1B) the $^{9,10}$AnBox$^{4+}$, (FIG. 1C) the $^{2,6}$AnBox$^{4+}$, and (FIG. 1D) the Anthracenec$^{2,6}$AnBox$^{4+}$. PF$_6^-$ counterions are omitted for the sake of clarity.

2A) without addition of $KPF_6$, and (FIG. 2B) in $CD_3CN$ solution saturated with $KPF_6$ (140 mM). FIG. 2C shows the schematic of dicationic intermediate insertion model $DM^{2+}$ into $^{2,6}AnBox^{4+}$.

FIGS. 3A-3D shows representations of the solid-state (super)structures of polymorphic $^{2,6}AnHC^{8+}$. The α-polymorph shown in FIG. 3A and FIG. 3B was obtained in the absence of $TBAPF_6$, whereas the β-polymorph shown in FIG. 3C and FIG. 3D was obtained in the presence of excess $TBAPF_6$. Space-filling representation of the α-polymorph (FIG. 3A) and β-polymorph (FIG. 3C) of $^{2,6}AnHC^{8+}$ structure. Stick representation of the α-polymorph (FIG. 3B) and β-polymorph (FIG. 3D) of $^{2,6}AnHC^{8+}$ superstructure.

(FIG. 5A) Absorption spectra of $^{2,6}AnDB^{2+}$ (1), $^{9,10}AnBox^{4+}$ (2), $^{2,6}AnBox^{4+}$ (3), and $^{2,6}AnHC^{8+}$ (4) in MeCN. (FIG. 5B) Gas-phase frontier orbitals of $^{9,10}AnBox^{4+}$ and $^{2,6}AnBox^{4+}$ cyclophanes.

(FIG. 6A) Normalized absorption spectra of $^{2,6}AnHC^{8+}$. (FIG. 6B) Normalized emission spectra of $^{2,6}AnBox^{4+}$ ($\lambda_{ex}$=450 nm). (FIG. 6C) Normalized emission spectra of $^{2,6}AnHC^{8+}$ ($\lambda_{ex}$=450 nm). (FIG. 6D) Lippert-Mataga solvatochromism plot of $^{2,6}AnCH^{8+}$ showing the relationship between the Stokes shifts (δ) and the orientation polarizability (Δf).

(FIG. 9A) Normalized absorption spectra. (FIG. 9B) Normalized emission spectra ($\lambda_{exc}$=450 nm)

(FIG. 10A) Concentration dependence of the $^{2,6}AnBox^{4+}$ in MeCN. (FIG. 10B) Concentration dependence of the $^{2,6}AnDB^{2+}$ in aqueous solution

DETAILED DESCRIPTION OF THE INVENTION

Figure 1A:
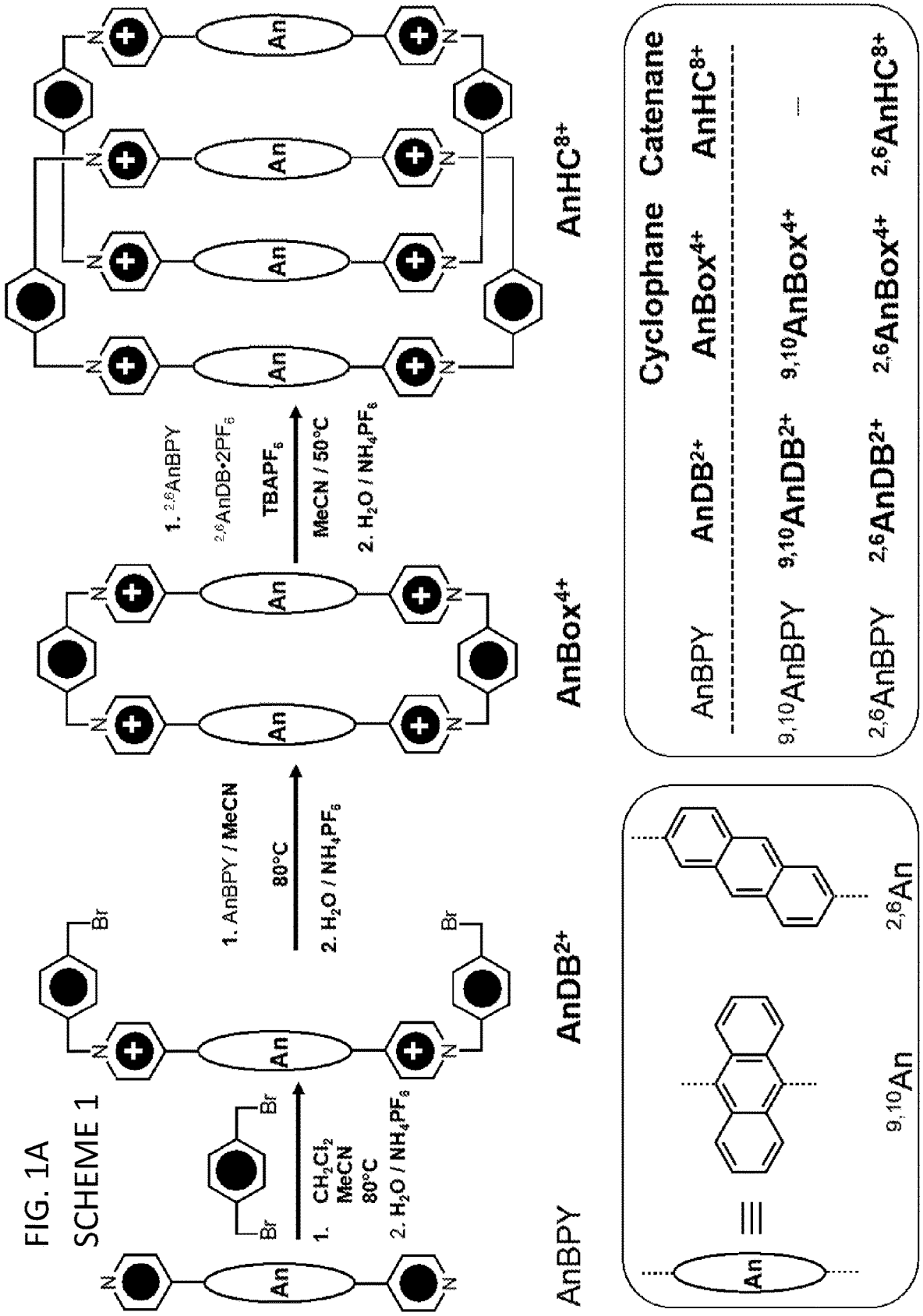
FIG. 1A shows the synthesis of the anthracene-based cyclophanes (AnBox$^{4+}$) and homo[2]catenane (AnHC$^{8+}$). PF$_6^-$ counterions are omitted for the sake of clarity.

Disclosed herein are methods for live-cell imaging, catenanes for performing the live cell imaging, and methods for making the catenanes. The catenanes for use in live cell imaging comprising two mechanically interlocked macrocycles. Each of the mechanically interlocked macrocycles comprise an aromatic fluorophore subunit and, by virtue of the mechanical bond, the aromatic fluorophores are arranged in a face-to-face [π . . . π] stack. This is turn allows for exciplex emission from within live cells at micromolar concentrations.

Mechanical bonds allow for the production of rigid and robust mechanically interlocked structures and mechanically interlaced superstructures by dint of a combination of both covalent and noncovalent bonding interactions, while maintaining precise arrangements of the components of mechanically interlocked molecules (MIMs) and complexes, respectively. Mechanical bonds also allow for confinement and the spatially restricted components which may led to the observation of circularly polarized luminescence (CPL) in solution and mechanochromic properties in the solid state. Moreover, mechanical bonds also allow for the fine tuning of the properties of the MIMs by introducing one or more functional groups. Catenanes are a class of MIMs which consist of two or more rings interconnected by mechanical bonds. Homo[2]catenanes are a class of catenanes, in which two constitutionally identical rings are mechanically interlocked. Although several flexible homo[2]catenanes using aliphatic chains have been reported, rigid homo[2]catenanes with well-defined shapes and co-conformations in solution and/or the solid state are few and far between. The rational design and syntheses of stable and rigid homo[2]catenanes remain a challenge, since they require the selection of self-complementary building unit(s) with strong inter-component binding in order to drive the self-templation of the catenanes.

Catenanes for use with the present technology include those that are comprised of two mechanically interlocked macrocycles where each of the macrocycles comprises an aromatic fluorophore subunit. As a result of mechanically interlocking the macrocycles, the aromatic fluorophores can be arranged in a face-to-face [π . . . π] stack allowing for the exciplex emission. Suitably, each of the macrocycles may comprise one or two aromatic fluorophore subunits and all of the aromatic fluorophore subunits of the catenane may be arranged in a face-to-face [π . . . π] stack. In some embodiments, the catenane has 2, 3, or 4 aromatic fluorophore subunits.

In one embodiment, the aromatic fluorophore subunit comprises an anthracene subunit. Anthracene is a polycyclic aromatic $C_{14}$ hydrocarbon having a linear arrangement of three aromatic rings. The anthracene subunit may be covalently bonded to the macrocycle at any two positions. Suitably, the anthracene is covalently bonded through the 2 and 6 positions, as demonstrated in the Examples. In some embodiments, the anthracene subunit may be covalently bonded to pyridine moieties, thereby forming a bipyridine anthracene subunit.

The anthracene subunit may be optionally substituted to tailor the photophysical properties of the anthracene subunit. Substituents may include, but are not limited to, $C_1$-$C_6$ alkyl, $C_1$-$C_6$ alkenyl, $C_1$-$C_6$ alkynyl, carboxy, carbonyl, aldehyde, $C_1$-$C_6$ alkoxy, —OH, —$NH_2$, —SH, —CN, —$NO_2$, —F, —$C_1$, —Br, or —I moieties.

The aromatic fluorophore subunits are linked through any linker capable of providing an appropriate spacing for the face-to-face [π . . . π] stacking necessary for exciplex emission. Suitably, the linker may be a xylylene subunit, such asp-xylylene. The xylylene subunits may be substituted. Exemplary substituents for the linker or xylylene subunit may include, but are not limited to, $C_1$-$C_6$ alkyl, $C_1$-$C_6$ alkenyl, $C_1$-$C_6$ alkynyl, carboxy, carbonyl, aldehyde, alkoxy, —OH, —$NH_2$, —SH, —CN, —$NO_2$, —F, —$C_1$, —Br, —I moieties.

Methods of using the catenanes described herein are provided for live cell imaging. The method may comprise contacting a cell with an effective amount of the catenane, irradiating the cell, and detecting exciplex emission from the catenane within the cell. MIA PACA2 prostate cancer cells were utilized in the Examples, but the presently disclosed methods are not limited to a particular type of cell. The cell may be any cell capable of taking up the catenane.

The effective amount of the catenane is an amount capable of being detected within the cell when irradiated. As demonstrated in the Examples, the catenane is capable of being detected at lower concentrations than an individual macrocycle. It is believed that this could be attributed to a higher effective charge and/or larger extinction coefficient. In some embodiments, effective amount of the catenane is about $10 \times 10^{-6}$ M or less, including $7.5 \times 10^{-6}$ M, $5.0 \times 10^{-6}$ M, or $2.5 \times 10^{-6}$ M or less.

The cell may be irradiated at any wavelength suitably for exciting the catenane within the cell. In some embodiments, the cell is irradiated with a wavelength of about 500 nm or less, including 475 nm, 450 nm, 425 nm, or 400 nm or less. The cell may be irradiated by methods and optical sources used for live cell fluorescent spectroscopy or microscopy.

The detected emission may be at any exciplex wavelength. In some embodiments, the detected emission is a wavelength of about 600 nm or more, including 625 nm, 650 nm, 675 nm, or 700 nm or less. The emission may be detected by methods and detection devices used for live cell fluorescent spectroscopy or microscopy.

The methods for live cell imaging may be performed in any suitable environment. In some embodiments, the methods are performed in vitro or ex vivo. In other embodiments, the methods are performed in vivo.

As demonstrated by the Examples, exciplex PL was obtained from permanent structures by incorporating anthracene moieties into pyridinium-containing mechanically interlocked molecules (MIMs). Beyond the optical properties of the anthracene moieties, their π-extended nature enforces [π . . . π] stacking that can overcome the Coulombic repulsion between the pyridinium units, affording an efficient synthesis of an octacationic homo[2]catenane. Notably, upon increasing the ionic strength by adding tetrabutylammonium hexafluorophosphate, the catenane yield increases significantly as a result of the decrease in Coulombic repulsions between the pyridinium units. As shown in the Examples, the ground state photophysical properties of the free cyclophane and the catenane may be similar and show a charge transfer band at 455 nm but their PL characters are distinct, denoting different excited states. The cyclophane emits at 562 nm (quantum yield $(\phi_F)$=3.6%, emission lifetime $\tau_s$=3 ns in MeCN), which characteristic of a disubstituted anthracene-pyridinium linker. By contrast, the catenane displays an exciplex PL at low concentration ($10^{-8}$ M) with an emission band centered on 650 nm ($\phi_F$=0.5%, $\tau_s$=14 ns) in MeCN and at 675 nm in aqueous solution. Live-cell imaging performed in MIAPaCa-2 prostate cancer cells confirmed that the catenane exciplex emission can be detected at micromolar concentrations.

Two synthetic approaches for the construction of highly charged homo[2]catenanes may be used. The first, exploits strong radical-radical interactions between 4,4-bipyridinium radical cations under reducing conditions to produce rigid octacationic homo[2]catenanes. The second allows for formation of an octacationic homo[2]catenane as a result of strong homophilic recognition between dicationic electron-rich aromatic units. The high charge densities in these homo[2]catenanes ensures better solubilities in both water and organic solvents, depending on the nature of the counterions. The generation of new homo[2]catenanes is hampered by synthetic challenges. Furthermore, the synthesis of homo[2]catenanes, containing two tetracationic macrocycles is energetically demanding and thermodynamically unfavorable. Such syntheses require favorable attractive templation that can counteract high Coulombic repulsions.

As demonstrated in the Examples, an electron-rich anthracene moiety is incorporated between two pyridinium units leading, not only to the emergence of push-pull charge transfer (CT) character, but also to favorable [π-π] interactions for the self-templating of a homo[2]catenane. FIG. 1A shows a scheme (Scheme 1) for the preparation of two anthracene-based tetracationic cyclophanes, $^{9,10}$AnBox$^{4+}$ and $^{2,6}$AnBox$^{4+}$, which incorporate two constitutional isomers, 9,10-bis-4-pyridyl-anthracene ($^{9,10}$AnBPY) and 2,6-bis-4-pyridyl-anthracene ($^{2,6}$AnBPY), respectively. While favorable host-guest interactions between the $^{2,6}$AnBox$^{4+}$ and the anthracene moiety lead to the homo[2]catenane $^{2,6}$AnHC$^{8+}$, the preparation of $^{9,10}$AnHC$^{8+}$ remains elusive as a result of the small and sterically hindered cavity of the $^{9,10}$AnBox$^{4+}$. The cyclophanes and the homo[2]catenane were characterized by mass spectrometry, single crystal X-ray diffraction (XRD), and $^1$H and $^{13}$C nuclear magnetic resonance (NMR) spectroscopies. In addition, absorption and fluorescence investigations were performed for $^{2,6}$AnHC$^{8+}$ in order to decipher the role of the mechanical bond in the persistence of the exciplex emission under highly dilute conditions. Finally, live-cell imaging, performed on MIAPaCa-2 prostate cancer cells, have demonstrated that the anthracene exciplex emission can be detected at micromolar concentrations.

Of two constitutionally isomeric cyclophanes, $^{9,10}$AnBox$^{4+}$ and $^{2,6}$AnBox$^{4+}$ with anthracene moieties inserted between two pyridinium units, $^{2,6}$AnBox$^{4+}$ has been found to host anthracene and its derivatives, e.g., $^{2,6}$AnDB$^{2+}$. The octacationic anthracene-based homo[2]catenane 2,6AnHC$^{8+}$, composed of two mechanically-interlocked $^{2,6}$AnBox$^{4+}$ boxes, was formed by the self-templating through [π . . . π] interactions between the $^{2,6}$AnBox$^{4+}$ cyclophane and its precursors, $^{2,6}$AnDB$^{2+}$ and $^{2,6}$AnBPY, particularly in the presence of excess of TBAPF$_6$. While the significant increase in the binding affinity of the dicationic $^{2,6}$AnDB$^{2+}$ in the presence of TBAPF$_6$ is conclusive evidence of the salt's role in attenuating the Coulombic repulsions between the pyridinium units, this salt also enhances the yield of the catenane quiet dramatically from 5 up to 40%. Polymorphs of the homo [2]catenane, exhibiting different co-conformations, were obtained depending on the absence or presence of the salt. A comparison of the absorption and luminescence properties of the cyclophanes and the homo[2]catenane revealed that the introduction of the mechanical bond results, at micromolar concentrations in acetonitrile solution, in persistent anthracene exciplex emission at 650 nm. Moreover, this emission is shifted to 675 nm in aqueous solution, offering a low energy, water-soluble fluorophore for bioimaging. Live-cell imaging, performed on MIA PaCa-2 prostate cancer cells, confirmed that the catenane exciplex emission can be detected at micromolar concentrations. These findings demonstrate that the incorporation of photoactive polyaromatic components like anthracene into cyclophanes can impart dual functionality, not only acting as a self-templating system for the formation of a mechanical bond, as in the synthesis of the homo[2]catenane, but also brings fluorophores into close enough contact to generate permanent exciplex emissions.

Definitions

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of a cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)N R^2 R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES 1. (a) Chan, J.; Dodani, S. C.; Chang, C. J., Reaction-Based Small-Molecule Fluorescent Probes for Chemoselective Bioimaging. *Nat. Chem.* 2012, 4, 973-984. (b) Sun, B.; Yang, X.; Ma, L.; Niu, C.; Wang, F.; Na, N.; Wen, J.; Ouyang, J., Design and Application of Anthracene Derivative with Aggregation-Induced Emission Charateristics for Visualization and Monitoring of Erythropoietin Unfolding. *Langmuir* 2013, 29, 1956-1962. (c) Chen, X.-M.; Chen, Y.; Yu, Q.; Gu, B.-H.; Liu, Y., Supramolecular Assemblies with Near-Infrared Emission Mediated in Two Stages by Cucurbituril and Amphiphilic Calixarene for Lysosome-Targeted Cell Imaging. *Angew. Chem. Int. Ed.* 2018, 57, 12519-12523.

2. (a) Ojida, A.; Mito-Oka, Y.; Inoue, M. A.; Hamachi, I., First Artificial Receptors and Chemosensors Toward Phosphorylated Peptide in Aqueous Solution. *J. Am. Chem. Soc.* 2002, 124, 6256-6258. (b) Ghosh, K.; Sarkar, A. R.; Masanta, G., An Anthracene Based Bispyridinium Amide Receptor for Selective Sensing of Anions. *Tetrahedron Lett.* 2007, 48, 8725-8729. (c) Lohani, C. R.; Kim, J.-M.; Lee, K.-H., Facile Synthesis of Anthracene-Appended Amino Acids as Highly Selective and Sensitive Fluorescent $Fe^{3+}$ Ion Sensors. *Bioorg. Med. Chem. Lett.* 2009, 19, 6069-6073. (d) Yoshizawa, M.; Klosterman, J. K., Molecular Architectures of Multi-Anthracene Assemblies. *Chem. Soc. Rev.* 2014, 43, 1885-1898. (e) Erdemir, S.; Kocyigit, O., Anthracene Excimer-Based "Turn On" Fluorescent Sensor for $Cr^{3+}$ and $Fe^{3+}$ Ions: Its Application to Living Cells. *Talanta* 2016, 158, 63-69. (f) Yoshizawa, M.; Catti, L., Bent Anthracene Dimers as Versatile Building Blocks for Supramolecular Capsules. *Acc. Chem. Res.* 2019, 52, 2392-2404.

3. (a) Wang, C.; Liu, Y.; Ji, Z.; Wang, E.; Li, R.; Jiang, H.; Tang, Q.; Li, H.; Hu, W., Cruciforms: Assembling Single Crystal Micro- and Nanostructures from One to Three Dimensions and their Applications in Organic Field-Effect Transistors. *Chem. Mater.* 2009, 21, 2840-2845. (b) Babu, S. S.; Hollamby, M. J.; Aimi, J.; Ozawa, H.; Saeki, A.; Seki, S.; Kobayashi, K.; Hagiwara, K.; Yoshizawa, M.; Möhwald, H.; Nakanishi, T., Nonvolatile Liquid Anthracenes for Facile Full-Colour Luminescence Tuning at Single Blue-Light Excitation. *Nat. Commun.* 2013, 4, 1969.

4. (a) Seo, B. M.; Seo, J. H.; Kim, J. H.; Park, J. S.; Lee, K. H.; Park, M. H.; Yoon, S. S.; Kim, Y. K., Efficient Orange-Red Organic Light-Emitting Diodes using 9,10-bis[4-(di-4-tert-butylphenylamino)styryl] Anthracene as a Fluorescent Orange-Red Emitter. *Thin Solid Films.* 2010, 518, 6214-6218. (b) Lee, K. H.; Kang, L. K.; Lee, J. Y.; Kang, S.; Jeon, S. O.; Yook, K. S.; Lee, J. Y.; Yoon, S. S., Molecular Engineering of Blue Fluorescent Molecules Based on Silicon End-Capped Diphenylaminofluorene Derivatives for Efficient Organic Light-Emitting Materials. *Adv. Funct. Mater.* 2010, 20, 1345-1358. (c) Song, J. Y.; Park, S. N.; Lee, S. J.; Kim, Y. K.; Yoon, S. S., Novel Fluorescent Blue-Emitting Materials Based on Anthracene-Fluorene Hybrids with Triphenylsilane Group for Organic Light-Emitting Diodes. *Dyes Pigm.* 2015, 114, 40-46.

5. (a) Hestand, N. J.; Spano, F. C., Expanded Theory of H- and J-Molecular Aggregates: The Effects of Vibronic Coupling and Intermolecular Charge Transfer. *Chem. Rev.* 2018, 118, 7069-7163. (b) Banerjee, S.; Both, A. K.; Sarkar, M., Probing the Aggregation and Signaling Behavior of Some Twisted 9,9'-Bianthryl Derivatives: Observation of Aggregation-Induced Blue-Shifted Emission. *ACS Omega* 2018, 3, 15709-15724. (c) Luo, J.; Qu, H.; Yin, J.; Zhang, X.; Huang, K.-W.; Chi, C., it-Conjugated Oligothiophene-Anthracene Co-Oligomers: Synthesis, Physical Properties, and Self-Assembly. *J. Mater. Chem.* 2009, 19, 8202-8211.

6. (a) Sugino, M.; Araki, Y.; Hatanaka, K.; Hisaki, I.; Miyata, M.; Tohnai, N., Elucidation of Anthracene Arrangement for Excimer Emission at Ambient Conditions. *Cryst. Growth Des.* 2013, 13, 4986-4992. (b) Shen, Y.; Liu, H.; Zhang, S.; Gao, Y.; Li, B.; Yan, Y.; Hu, Y.; Zhao, L.; Yang, B., Discrete Face-to-Face Stacking of Anthracene Inducing High-Efficiency Excimer Fluorescence in Solids via a Thermally Activated Phase Transition. *J. Mater. Chem. C* 2017, 5, 10061-10067.

7. Lehmann, M.; Gloza, S.; Roth, S., At the Limits of Liquid Crystallinity: Stimuli Responsive 3D Columnar Liquid Crystals and Soft Crystals of Supramolecular Anthracene Mesogens. *Chem. Mater.* 2015, 27, 8181-8184.

8. Chen, Z.; Lohr, A.; Saha-Möller, C. R.; Würthner, F., Self-Assembled π-Stacks of Functional Dyes in Solution: Structural and Thermodynamic Features. *Chem. Soc. Rev.* 2009, 38, 564-584.

9. Beldjoudi, Y.; Arauzo, A.; Campo, J.; Gavey, E. L.; Pilkington, M.; Nascimento, M. A.; Rawson, J. M., Structural, Magnetic, and Optical Studies of the Polymorphic 9'-Anthracenyl Dithiadiazolyl Radical. *J. Am. Chem. Soc.* 2019, 141, 6875-6889.

10. Dimitriev, O. P.; Piryatinski, Y. P.; Slominskii, Y. L., Abnormal Emission in the Heterogeneous J-Aggregate System. *J. Phys. Chem. C.* 2019, 123, 28611-28619.

11. Musser, A. J.; Rajendran, S. K.; Georgiou, K.; Gai, L.; Grant, R. T.; Shen, Z.; Cavazzini, M.; Ruseckas, A.; Turnbull, G. A.; Samuel, I. D. W.; Clark, J.; Lidzey, D. G., Intermolecular States in Organic Dye Dispersions: Excimers vs. Aggregates. *J. Mater. Chem.* 2017, 5, 8380-8389.

12. (a) Liu, H.; Yao, L.; Li, B.; Chen, X.; Gao, Y.; Zhang, S.; Li, W.; Lu, P.; Yang, B.; Ma, Y., Excimer-Induced High-Efficiency Fluorescence due to Pairwise Anthracene Stacking in a Crystal with Long Lifetime. *Chem. Comm.* 2016, 52, 7356-7359. (b) Vollbrecht, J., Excimers in Organic Electronics. *New J. Chem.* 2018, 42, 11249-11254.

13. Fleetham, T.; Ji, Y.; Huang, L.; Fleetham, T. S.; Li, J., Efficient and Stable Single-Doped White OLEDs Using a Palladium-Based Phosphorescent Excimer. *Chem. Sci.* 2017, 8, 7983-7990.

14. Santiago-Gonzalez, B.; Monguzzi, A.; Azpiroz, J. M.; Prato, M.; Erratico, S.; Campione, M.; Lorenzi, R.; Pedrini, J.; Santambrogio, C.; Torrente, Y.; De Angelis, F.; Meinardi, F.; Brovelli, S., Permanent Excimer Superstructures by Supramolecular Networking of Metal Quantum Clusters. *Science* 2016, 353, 571-575.

15. a) Birks, J. B.; Christophorou, L. G., Excimer Formation in Polycyclic Hydrocarbons and their Derivatives. *Nature* 1963, 197, 1064-1065. (b) Barnes, R. L.; Birks, J. B.; Flowers, B. H., 'Excimer' Fluorescence-X. Spectral Studies of 9-Methyl and 9, 10-Dimethyl Anthracene. *Proc. R. Soc. Lond.* 1966, 291, 570-582. (c) McVey, J. K.; Shold, D. M.; Yang, N. C., Direct Observation and Characterization of Anthracene Excimer in Solution. *Chem. Phys.* 1976, 65, 3375-3376. (d) Luo, J.; Qu, H.; Yin, J.; Zhang, X.; Huang, K.-W.; Chi, C., π-Conjugated oligothiophene-anthracene co-oligomers: synthesis, physical properties, and self-assembly. *J. Mater. Chem.* 2009, 19, 8202-8211. (e) Osaki, H.; Chou, C.-M.; Taki, M.; Welke, K.; Yokogawa, D.; Irle, S.; Sato, Y.; Higashiyama, T.; Saito, S.; Fukazawa, A.; Yamaguchi, S., A Macrocyclic Fluorophore Dimer with Flexible Linkers: Bright Excimer Emission with a Long Fluorescence Lifetime. *Angew. Chem.* 2016, 55, 7131-7135.

16. (a) Chen, K.-H.; Yang, J.-S.; Hwang, C.-Y.; Fang, J.-M., Phospholipid-Induced Aggregation and Anthracene Excimer Formation. *Org. Lett.* 2008, 10, 4401-4404. (b) Nandajan, P. C.; Neelakandan, P. P.; Ramaiah, D., Interplay of Monomer, Intra- and Intermolecular Excimer Fluorescence in Cyclophanes and Selective Recognition of Methanol Vapours. *RSC Adv.* 2013, 3, 5624-5630. (c) Uttam, B.; Chawla, H. M.; Pant, N.; Shahid, M., Proficient Molecular Receptor Exhibiting "On-Off" Excimer Fluorescence with Fluoride and Mercury Toxicants. *J. Photochem. Photobiol.* 2017, 349, 224-229.

17. Gao, Y.; Liu, H.; Zhang, S.; Gu, Q.; Shen, Y.; Ge, Y.; Yang, B., Excimer Formation and Evolution of Excited State Properties in Discrete Dimeric Stacking of an Anthracene Derivative: A Computational Investigation. *Phys. Chem. Chem. Phys.* 2018, 20, 12129-12137.

18. (a) Bouas-Laurent, H.; Castellan, A.; Desvergne, J.-P.; Lapouyade, R., Photodimerization of Anthracenes in Fluid Solution: Structural Aspects. *Chem. Soc. Rev.* 2000, 29, 43-55. (b) Bouas-Laurent, H.; Castellan, A.; Desvergne, J.-P.; Lapouyade, R., Photodimerization of anthracenes in Fluid Solutions: (Part 2) Mechanistic Aspects of the Photocycloaddition and of The Photochemical and Thermal Cleavage. *Chem. Soc. Rev.* 2001, 30, 248-263.

19. (a) Chen, J.; Neels, A.; Fromm, K. M., Excimer Formation in Crystalline and Nanostructured Coordination Polymers. *Chem. Comm.* 2010, 46, 8282-8284. (b) Zhang, G.; Yang, G.; Wang, S.; Chen, Q.; Ma, J. S., A Highly Fluorescent Anthracene-Containing Hybrid Material Exhibiting Tunable Blue-Green Emission Based on the Formation of an Unusual "T-Shaped" Excimer. *Chem. Eur. J.* 2007, 13, 3630-3635. (c) Zhao, C.; Cai, X.; Ma, Z.; Shi, J.; Xu, L.; Wang, H., Excimer Formation from Particially Overlapped Anthracene Dimer Based on Saddle-Shaped Cyclooctatetrathiophene as Spacer. *J. Photochem. Photobiol.* 2018, 355, 318-325.

20. Lekha, P. K.; Prasad, E., Aggregation-Controlled Excimer Emission from Anthracene-Containing Polyamidoamine Dendrimers. *Chem. Eur. J.* 2010, 16, 3699-3706.
21. Amicangelo, J. C.; Leenstra, W. R., Excimer Formation in the Interlayer Region of Arene-Derivatized Zirconium Phosphonates. *J. Am. Chem. Soc.* 2003, 125, 14698-14699.
22. (a) Kwon, 0.-H.; Yu, H.; Jang, D.-J., Formation Mechanism of Anthracene Dimers and Excimers in NaY Zeolitic Nanocavities. *J. Phys. Chem. B.* 2004, 108, 3970-3974. (b) Kaanumalle, L. S.; Gibb, C. L. D.; Gibb, B. C.; Ramamurthy, V., A Hydrophobic Nanocapsule Controls the Photophysics of Aromatic Molecules by Suppressing Their Favored Solution Pathways. *J. Am. Chem. Soc.* 2005, 127, 3674-3675.
23. (a) Stoddart, J. F., Mechanically Interlocked Molecules (MIMs)-Molecular Shuttles, Switches, and Machines (Nobel Lecture). *Angew. Chem. Int. Ed.* 2017, 56, 11094-11125. (b) Sauvage, J.-P., From Chemical Topology to Molecular Machines (Nobel Lecture). *Angew. Chem. Int. Ed.* 2017, 56, 11080-11093.
24. (a) Juriček, M.; Barnes, J. C.; Strutt, N. L.; Vermeulen, N. A.; Ghooray, K. C.; Dale, E. J.; McGonigal, P. R.; Blackburn, A. K.; Avestro, A.-J.; Stoddart, J. F., An ExBox[2]Catenane. *Chem. Sci.* 2014, 5, 2724-2731. (b) Ryan, S. T. J.; Young, R. M.; Henkelis, J. J.; Hafezi, N.; Vermeulen, N. A.; Hennig, A.; Dale, E. J.; Wu, Y.; Krzyaniak, M. D.; Fox, A.; Nau, W. M.; Wasielewski, M. R.; Stoddart, J. F.; Scherman, O. A., Energy and Electron Transfer Dynamics within a Series of Perylene Diimide/Cyclophane Systems. *J. Am. Chem. Soc.* 2015, 137, 15299-15307.
25. (a) Inouye, M.; Hayashi, K.; Yonenaga, Y.; Itou, T.; Fujimoto, K.; Uchida, T.-A.; Iwamura, M.; Nozaki, K., A Doubly Alkynylpyrene-Threaded [4]Rotaxane That Exhibits Strong Circularly Polarized Luminescence from the Spatially Restricted Excimer. *Angew. Chem. Int. Ed.* 2014, 53, 14392-14396. (b) Hayashi, K.; Miyaoka, Y.; Ohishi, Y.; Uchida, T.-A.; Iwamura, M.; Nozaki, K.; Inouye, M., Observation of Circularly Polarized Luminescence of the Excimer from Two Perylene Cores in the Form of [4]Rotaxane. *Chem. Eur. J.* 2018, 24, 14613-14616. (c) David, A. H. G.; Casares, R.; Cuerva, J. M.; Campaña, A. G.; Blanco, V., A [2]Rotaxane-Based Circularly Polarized Luminescence Switch. *J. Am. Chem. Soc.* 2019, 141, 18064-18074.
26. (a) Sagara, Y.; Karman, M.; Verde-Sesto, E.; Matsuo, K.; Kim, Y.; Tamaoki, N.; Weder, C., Rotaxanes as Mechanochromic Fluorescent Force Transducers in Polymers. *J. Am. Chem. Soc.* 2018, 140, 1584-1587. (b) Sagara, Y.; Karman, M.; Seki, A.; Pannipara, M.; Tamaoki, N.; Weder, C., Rotaxane-Based Mechanophores Enable Polymers with Mechanically Switchable White Photoluminescence. *ACS Cent. Sci.* 2019, 5, 874-881.
27. (a) Stoddart, J. F., The Chemistry of the Mechanical Bond. *Chem. Soc. Rev.* 2009, 38, 1802-20. (b) Neal, E. A.; Goldup, S. M., Chemical Consequences of Mechanical Bonding in Catenanes and Rotaxanes: Isomerism, Modification, Catalysis and Molecular Machines for Synthesis. *Chem. Comm.* 2014, 50, 5128-5142.
28. (a) Evans, N. H.; Beer, P. D., Progress in the Synthesis and Exploitation of Catenanes Since the Millennium. *Chem. Soc. Rev.* 2014, 43, 4658-4683. (b) Gil-Ramirez, G.; Leigh, D. A.; Stephens, A. J Catenanes: Fifty Years of Molecular Links. *Angew. Chem. Int. Ed.* 2015, 54, 6110-6150. (c) Au-Yeung, H. Y.; Yee, C.-C.; Hung Ng, A. W.; Hu, K., Strategies to Assemble Catenanes with Multiple Interlocked Macrocycles. *Inorg. Chem.* 2018, 57, 3475-3485.
29. (a) Dietrich-Buchecker, C. O.; Sauvage, J.-P.; Kern, J. M., Templated Synthesis of Interlocked Macrocyclic Ligands: The Catenands. *J. Am. Chem. Soc.* 1984, 106, 3043-3045. (b) Wang, W.; Wang, L.; Palmer, B. J.; Exarhos, G. J.; Li, A. D. Q., Cyclization and Catenation Directed by Molecular Self-Assembly. *J. Am. Chem. Soc.* 2006, 128, 11150-11159. (c) Theil, A.; Mauve, C.; Adeline, M.-T.; Marinetti, A.; Sauvage, J.-P., Phosphorus-Containing [2]Catenanes as an Example of Interlocking Chiral Structures. *Angew. Chem. Int. Ed.* 2006, 45, 2104-2107. (d) Chae, M. K.; Suk, J.-m.; Jeong, K.-S., A Catenated Anion Receptor Based on Indolocarbazole. *Tetrahedron Lett.* 2010, 51, 4240-4242. (e) Caballero, A.; Zapata, F.; White, N. G.; Costa, P. J.; Felix, V.; Beer, P. D., A Halogen-Bonding Catenane for Anion Recognition and Sensing. *Angew. Chem. Int. Ed.* 2012, 51, 1876-1880. (f) Mitra, R.; Thiele, M.; Octa-Smolin, F.; Letzel, M. C.; Niemeyer, J., A Bifunctional Chiral [2]Catenane Based on 1,1'-Binaphthyl-Phosphates. *Chem. Comm.* 2016, 52, 5977-5980. (g) Wu, G.; Wang, C.-Y.; Jiao, T.; Zhu, H.; Huang, F.; Li, H., Controllable Self-Assembly of Macrocycles in Water for Isolating Aromatic Hydrocarbon Isomers. *J. Am. Chem. Soc.* 2018, 140, 5955-5961. (h) Wang, C.-Y.; Wu, G.; Jiao, T.; Shen, L.; Ma, G.; Pan, Y.; Li, H., Precursor Control Over the Self-Assembly of [2]Catenanes via Hydrazone Condensation in Water. *Chem. Comm.* 2018, 54, 5106-5109.
30. (a) Hunter, C. A., Synthesis and Structure Elucidation of a New [2]-Catenane. *J. Am. Chem. Soc.* 1992, 114, 5303-5311. (b) Vögtle, F.; Meier, S.; Hoss, R., One-Step Synthesis of a Fourfold Functionalized Catenane. Angew. Chem. Int. Ed. 1992, 31, 1619-1622. (c) Johnston, A. G.; Leigh, D. A.; Pritchard, R. J.; Deegan, M. D., Facile Synthesis and Solid-State Structure of a Benzylic Amide [2]Catenane. *Angew. Chem. Int. Ed.* 1995, 34, 1209-1212. (d) Johnston, A. G.; Leigh, D. A.; Nezhat, L.; Smart, J. P.; Deegan, M. D., Structurally Diverse and Dynamically Versatile Benzylic Amide [2]Catenanes Assembled Directly from Commercially Available Precursors. *Angew. Chem. Int. Ed.* 1995, 34, 1212-1216. (e) Mehta, G.; Srinivas, K.; Vidya, R.; Uma, R.; Kunwar, A. C.; Ravi Kumar, K.; Vairamani, M., Triquinane-Derived Macrocyclic Lactones and a [2]-Catenane: Synthesis and Characterization. *Tetrahedron* 1998, 54, 10879-10890.
31. (a) Griffiths Kirsten, E.; Stoddart, J. F., Template-Directed Synthesis of Donor/Acceptor [2]Catenanes and [2]Rotaxanes. *Pure Appl. Chem.* 2008, 80, 485-506. (b) Stoddart, J. F., The Chemistry of the Mechanical Bond. *Chem. Soc. Rev.* 2009, 38, 1802-1820. (c) Barin, G.; Coskun, A.; Fouda, M. M. G.; Stoddart, J. F., Mechanically Interlocked Molecules Assembled by π-π Recognition. *ChemPlusChem.* 2012, 77, 159-185.
32. (a) Trabolsi, A.; Khashab, N.; Fahrenbach, A. C.; Friedman, D. C.; Colvin, M. T.; Coti, K. K.; Benitez, D.; Tkatchouk, E.; Olsen, J.-C.; Belowich, M. E.; Carmielli, R.; Khatib, H. A.; Goddard, III. W. A.; Wasielewski, M. R.; Stoddart, J. F., Radically Enhanced Molecular Recognition. *Nat. Chem.* 2010, 2, 42-49. (b) Wang, Y.; Frasconi, M.; Stoddart, J. F., Introducing Stable Radicals into Molecular Machines. *ACS Cent. Sci.* 2017, 3, 927-935.
33. (a) Barnes, J. C.; Fahrenbach, A. C.; Cao, D.; Dyar, S. M.; Frasconi, M.; Giesener, M. A.; Benitez, D.; Tkatchouk, E.; Chernyashevskyy, O.; Shin, W. H.; Li, H.;

Sampath, S.; Stern, C. L.; Sarjeant, A. A.; Hartlieb, K. J.; Liu, Z.; Carmieli, R.; Botros, Y. Y.; Choi, J. W.; Slawin, A. M. Z.; Ketterson, J. B.; Wasielewski, M. R.; Goddard III. W. A.; Stoddart, J. F., A Radically Configurable Six-State Compound. *Science* 2013, 339, 429-433. (b) Barnes, J. C.; Frasconi, M.; Young, R. M.; Khdary, N. H.; Liu, W.-G.; Dyar, S. M.; McGonigal, P. R.; Gibbs-Hall, I. C.; Diercks, C. S.; Sarjeant, A. A.; Stern, C. L.; Goddard III. W. A.; Wasielewski, M. R.; Stoddart, J. F., Solid-State Characterization and Photoinduced Intramolecular Electron Transfer in a Nanoconfined Octacationic Homo[2] Catenane. *J. Am. Chem. Soc.* 2014, 136, 10569-10572. (c) Sun, J.; Liu, Z.; Liu, W.-G.; Wu, Y.; Wang, Y.; Barnes, J. C.; Hermann, K. R.; Goddard III. W. A; Wasielewski, M. R.; Stoddart, J. F., Mechanical-Bond-Protected, Air-Stable Radicals. *J. Am. Chem. Soc.* 2017, 139, 12704-12709.

34. Gong, X.; Zhou, J.; Hartlieb, K. J.; Miller, C.; Li, P.; Farha, O. K.; Hupp, J. T.; Young, R. M.; Wasielewski, M. R.; Stoddart, J. F., Toward a Charged Homo[2]catenane Employing Diazaperopyrenium Homophilic Recognition. *J. Am. Chem. Soc.* 2018, 140, 6540-6544.

35. Barnes, J. C.; Juriček, M.; Strutt, N. L.; Frasconi, M.; Sampath, S.; Giesener, M. A.; McGrier, P. L.; Bruns, C. J.; Stern, C. L.; Sarjeant, A. A.; Stoddart, J. F., ExBox: A Polycyclic Aromatic Hydrocarbon Scavenger. *J. Am. Chem. Soc.* 2013, 135, 183-192.

36. Ronson, T. K.; Meng, W.; Nitschke, J. R., Design Principles for the Optimization of Guest Binding in Aromatic-Paneled $Fe^{II}_4L_6$ Cages. *J. Am. Chem. Soc.* 2017, 139, 9698-9707.

37. Fujita, M.; Ibukuro, F.; Hagihara, H.; Ogura, K., Quantitative Self-Assembly of a [2]Catenane from Two Preformed Molecular Rings. *Nature* 1994, 367, 720-723.

38. Bruns, C. J.; Fujita, D.; Hoshino, M.; Sato, S.; Stoddart, J. F.; Fujita, M., Emergent Ion-Gated Binding of Cationic HostGuest Complexes Within Cationic $M_{12}L_{24}$ Molecular Flasks. *J. Am. Chem. Soc.* 2014, 136, 12027-12034.

39. (a) Conformational polymorphism is not uncommon in organic crystals and occurs when different conformers of the same molecule occur in different crystal forms. (b) Nangia, A., Conformational Polymorphism in Organic Crystals. *Acc. Chem. Res.* 2008, 41, 595-604.

40. Gaigalas, A. K.; Li, L.; Henderson, O.; Vogt, R.; Barr, J.; Marti, G.; Weaver, J.; Schwartz, A., The Development of Fluorescence Intensity Standards. *J. Res. Natl. Inst. Stand. Technol.* 2001, 106, 381-389.

41. Vasylevskyi, S. I.; Bassani, D. M.; Fromm, K. M., Anion-Induced Structural Diversity of Zn and Cd Coordination Polymers Based on Bis-9,10-(pyridine-4-yl)-anthracene, Their Luminescent Properties, and Highly Efficient Sensing of Nitro Derivatives and Herbicides. *Inorg. Chem.* 2019, 58, 5646-5653.

42. Baba, M.; Saitoh, M.; Taguma, K.; Shinohara, K.; Yoshida, K.; Semba, Y.; Kasahara, S.; Nakayama, N.; Goto, H.; Ishimoto, T.; Nagashima, U., Structure and Excited-State Dynamics of Anthracene: Ultrahigh-Resolution Spectroscopy and Theoretical Calculation. *J. Chem. Phys.* 2009, 130, 134315-134325.

43. Hou, Y.; Zhang, X.; Chen, K.; Liu, D.; Wang, Z.; Liu, Q.; Zhao, J.; Barbon, A., Charge Separation, Charge Recombination, Long-Lived Charge Transfer State Formation and Intersystem Crossing in Organic Electron Donor/Acceptor Dyads. *J. Mater. Chem. C* 2019, 7, 12048-12074.

44. Crystallographic investigations reveal the existence of [π . . . π] interactions between the anthracene units, while the $^1$H NMR spectroscopic studies show a significant upfield shift of the resonance of the anthracene proton as a result of [π . . . π] interactions.

45. Wu, Y.; Zhou, J.; Phelan, B. T.; Mauck, C. M.; Stoddart, J. F.; Young, R. M.; Wasielewski, M. R.Probing Distance Dependent Charge-Transfer Character in Excimers of Extended Viologen Cyclophanes Using Femtosecond Vibrational Spectroscopy. *J. Am. Chem. Soc.* 2017, 139, 14265-14276.

46. J. R. Lakowicz, Principles of Fluorescence Spectroscopy, *Springer, New York.* 2006.

47. Daze, K. and Hof, F. (2016). Molecular Interaction and Recognition. In Encyclopedia of Physical Organic Chemistry (eds Z. Wang, U. Wille and E. Juaristi). doi:10.1002/9781118468586.epoc3001.

48. Roy, I.; Bobbala, S.; Zhou, J.; Nguyen, M. T.; Nalluri, S. K. M.; Wu, Y.; Ferris, D. P.; Scott, E. A.; Wasielewski, M. R.; Stoddart, J. F., ExTzBox: A Glowing Cyclophane for Live-Cell Imaging. *J. Am. Chem. Soc.* 2018, 140, 7206-7212.

49. Liu, H.-W.; Xu, S.; Wang, P.; Hu, X.-X.; Zhang, J.; Yuan, L.; Zhang, X.-B.; Tan, W., An Efficient Two-photon Fluorescent Probe for Monitoring Mitochondrial Singlet Oxygen in Tissues During Photodynamic Therapy. *Chem. Comm.* 2016, 52, 12330-12333.

50. Roy, I.; Bobbala, S.; Young, R. M.; Beldjoudi, Y.; Nguyen, M. T.; Cetin, M. M.; Cooper, J. A.; Allen, S.; Anamimoghadam, O.; Scott, E. A.; Wasielewski, M. R.; Stoddart, J. F., A Supramolecular Approach for Modulated Photoprotection, Lysosomal Delivery, and Photodynamic Activity of a Photosensitizer. *J. Am. Chem. Soc.* 2019, 141, 12296-12304.

Examples

Synthesis and characterization of $^{9,10}$AnBox.4PF$_6$ Synthesis of the cyclophane $^{9,10}$AnBox.4PF$_6$ followed a one-pot strategy in which the isolated $^{9,10}$AnDB.2PF$_6$ was reacted (FIG. 1A) with $^{9,10}$AnBPY in the presence of catalytic amounts of tetrabutylammonium iodide (~20 mol %) in MeCN under reflux for 48 h. The pure cyclophane was obtained in 25% yield after counterion exchange with NH$_4$PF$_6$. See Schemes 2 and 3. Single crystals, suitable for X-ray crystallography, were obtained by vapor diffusion of i-Pr$_2$O into an MeCN solution of $^{9,10}$AnBox.4PF$_6$ over the course of one week. The solid-state structure (FIG. 1B) of the $^{9,10}$AnBox$^{4+}$ reveals a distorted box-like geometry as the result of the large twist angles between the anthracene and the two pyridinium units at the 9- and 10-positions. The torsional angles of 82° and 85° between the anthracene and pyridinium units are much higher than the average torsional angle)(~30° between the phenylene and the two pyridinium units observed [35] in the original ExBox$^{4+}$. In addition, the two anthracene units are oriented parallel to each other and are perpendicular to the plane of the pyridinium units with a shorter interplanar distance of 3.5 Å, indicating the presence of strong [π . . . π] interactions in $^{9,10}$AnBox$^{4+}$. The cyclophane is characterized by a small cavity measuring 5.7 Å in length and 5.8 Å in width. Analysis of the molecular packing reveals that the distorted nature of $^{9,10}$AnBox$^{4+}$ prevents the long-range propagation of the [π . . . π] interactions along the one direction. In solution, the $^1$H NMR spectrum of $^{9,10}$AnBox$^{4+}$ in CD$_3$CN shows that the resonances of the anthracene protons are shifted significantly upfield to δ=7.1 and 6.8 ppm, compared with those near δ=7.5 ppm for $^{9,10}$AnDB$^{2+}$. The chemical shifts of the resonances in the $^1$H NMR spectrum are to be expected because of the π-electron shielding effects of the anthracene on account of close [π . . . π] stacking. The strong [π . . . π] interactions have a profound effect on the cavity size and geometry of $^{9,10}$AnBox$^{4+}$, and hinder its ability to accommodate $^{9,10}$AnBPY and/or $^{9,10}$AnDB$^{2+}$ prior to catenane formation. Consequently, many attempts to synthesize the octacationic homo[2]catenane proved to be unsuccessful.

Synthesis, characterization, and host-guest properties of $^{2,6}$AnBox$^{4+}$

In order to favor the formation of a homo[2]catenane, we anticipated that the linear and rigid $^{2,6}$AnBPY could provide a cyclophane ($^{2,6}$AnBox$^{4+}$) with extended it-surfaces, which could engage in strong [π . . . π] interactions with its precursors. The synthesis of $^{2,6}$AnBox.4PF$_6$ followed a similar synthetic route to that of the $^{9,10}$AnBox.4PF$_6$ analogue. Moreover, using pyrene as a template during the synthesis improved the yield from 15 to 25%. See Schemes 5.

High-quality single crystals of $^{2,6}$AnBox$^{4+}$ were obtained by the slow vapor diffusion of i-Pr$_2$O into an MeCN solution of $^{2,6}$AnBox.4PF$_6$ over a period of one week. $^{2,6}$AnBox$^{4+}$ crystallizes in the orthorhombic Ccce space group with half a molecule in the asymmetric unit, leading therefore to a symmetrical box-like cyclophane in the solid state (FIG. 3B) measuring 18.8 Å in length and 6.5 and 7.6 Å in width at its periphery and center, respectively. Also, $^{2,6}$AnBox$^{4+}$ presents a larger cavity size (7.6 Å in width and 18.8 Å in length) compared to that in $^{9,10}$AnBox$^{4+}$. The torsional angles between the pyridinium and anthracene units of 18° are significantly smaller when compared to those found in $^{9,10}$AnBox$^{4+}$. The more rigid and symmetrical nature of $^{2,6}$AnBox$^{4+}$ leads to the [π . . . π] stacking of the cyclophanes along the a-axis as the result of the interaction of the anthracene moiety with the pyridinium unit. Density functional theory (DFT) calculations of the molecular electrostatic potential (MEP) of the $^{2,6}$AnBox$^{4+}$ reveal that the anthracene unit has a negative charge density while the pyridinium units possess a positive potential (data not shown). Therefore, donor-acceptor (DA) CT interactions are structure-directing in the 1D stacking of the cyclophanes along the a-axis. Along the b-axis, $^{2,6}$AnBox$^{4+}$ does not form a tubular superstructure as a result of the twist of the two cyclophanes from face-to-face interactions. The distance between the cyclophanes is irregular with alternating long and short distances forming pairs of dimers.

The cavity of $^{2,6}$AnBox$^{4+}$ is able to bind an anthracene molecule in a face-to-face manner as a result of [π . . . π] interactions. The formation of anthracene ⊂ $^{2,6}$AnBox$^{4+}$ (An ⊂ $^{2,6}$AnBox$^{4+}$) was confirmed by $^1$H NMR titration in CD$_3$CN. Significant upfield shifts of the resonances of the anthracene protons in $^{2,6}$AnBox$^{4+}$ are observed (data not shown) and were used to determine an association constant of K$_a$=125 M$^{-1}$. Further evidence for the formation of the 1:1 complex (anthracene ⊂ $^{2,6}$AnBox$^{4+}$) came from XRD analysis. The solid-state superstructure of the inclusion complex shows that the anthracene component is well positioned inside the $^{2,6}$AnBox$^{4+}$ cyclophane with complete [π . . . π] overlaps with the extended anthracene-based bipyridinium ($^{2,6}$AnBPY$^{2+}$) units. It is remarkable that, upon addition of the anthracene guest to the cavity of $^{2,6}$AnBox$^{4+}$, a tubular superstructure is formed along the c-axis, whereas along the b-axis, face-to-face [π . . . π] stacks form between the anthracene units. Apparently, the long-range [π . . . π] distances of 3.5 Å between the anthracene units are superstructure-directing in anthracene ⊂ $^{2,6}$AnBox$^{4+}$ instead of the anthracene-pyridinium DA interactions. The formation of the anthracene ⊂ $^{2,6}$AnBox$^{4+}$ complex implies that [π . . . π] interactions between the anthracene units can be sufficient to overcome the Coulombic repulsion and form the homo [2]catenane, $^{2,6}$AnHC.8PF$_6$.

Synthesis and Characterization of the $^{2,6}$AnHC.8PF$_6$ Homo [2]Catenane

Preparation of $^{2,6}$AnHC.8PF$_6$ was achieved following two synthetic procedures which consisted of mixing $^{2,6}$AnBox. 4PF$_6$ with its precursors $^{2,6}$AnDB.2PF$_6$, and $^{2,6}$AnBPY in the absence (Protocol I) or presence (Protocol II) of tetrabutylammonium hexafluorophosphate (TBAPF$_6$). See Scheme 6. Our attempts to prepare $^{2,6}$AnHC.8PF$_6$ following Protocol I produced very low yields (<5%) of the catenane. The binding constant, determined by $^1$H NMR titrations in CD$_3$CN, between anthracene and the $^{2,6}$AnBox$^{4+}$ cavity was found to be K$_a$=125 M$^{-1}$, whereas the affinities of the monocationic MM$^+$ (data not show) and the dicationic $^{2,6}$AnDB$^{2+}$ (data not shown) derivatives decrease (K$_a$=102 M$^{-1}$ and K$_a$=42 M$^{-1}$, respectively) as the charge number increases in concert with increased Coulombic repulsion.

Figure 2A:
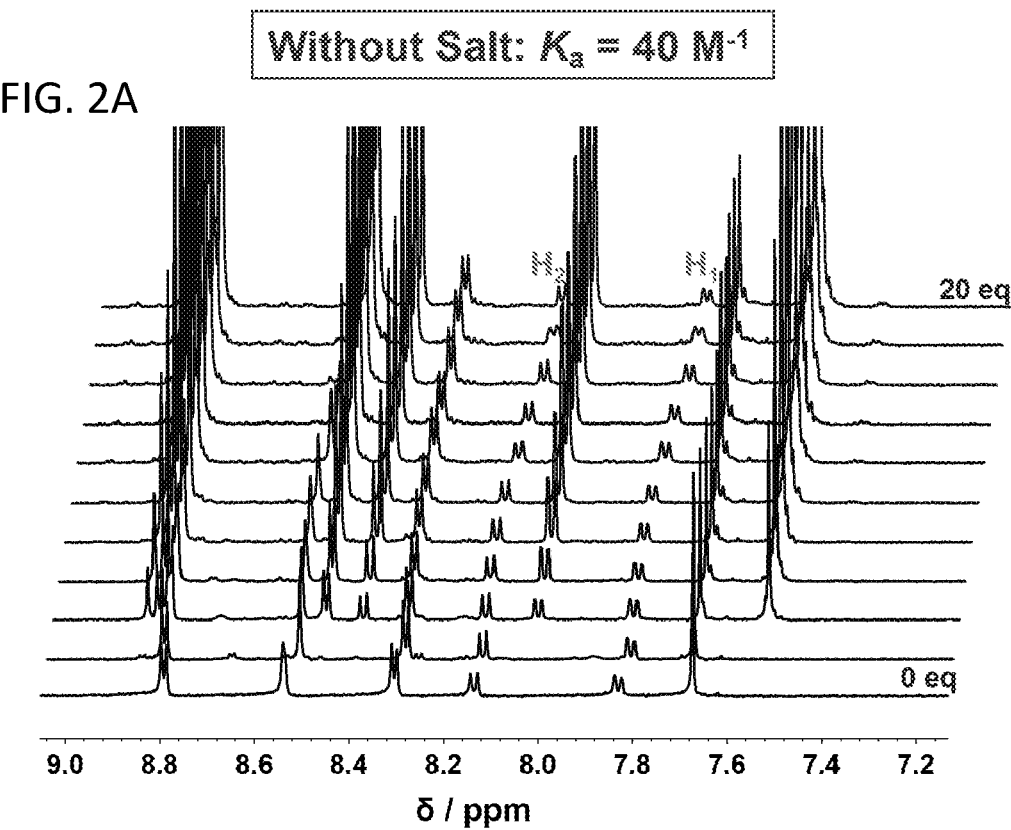
FIGS. 2A-2C shows $^1$H NMR titration of dicationic intermediate model DM$^{2+}$ into $^{2,6}$AnBox$^{4+}$ with increasing concentration of DM$^{2+}$ (600 MHz, CD$_3$CN, 298 K), (FIG.
Figure 2B:
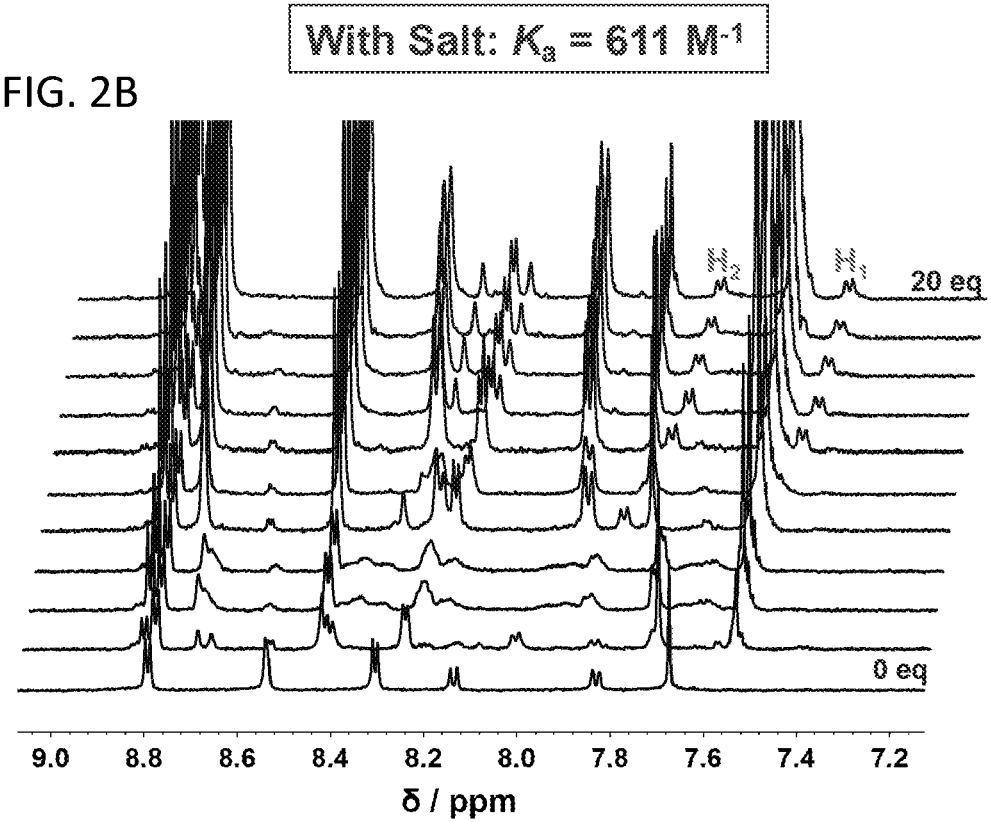
Figure 2C:
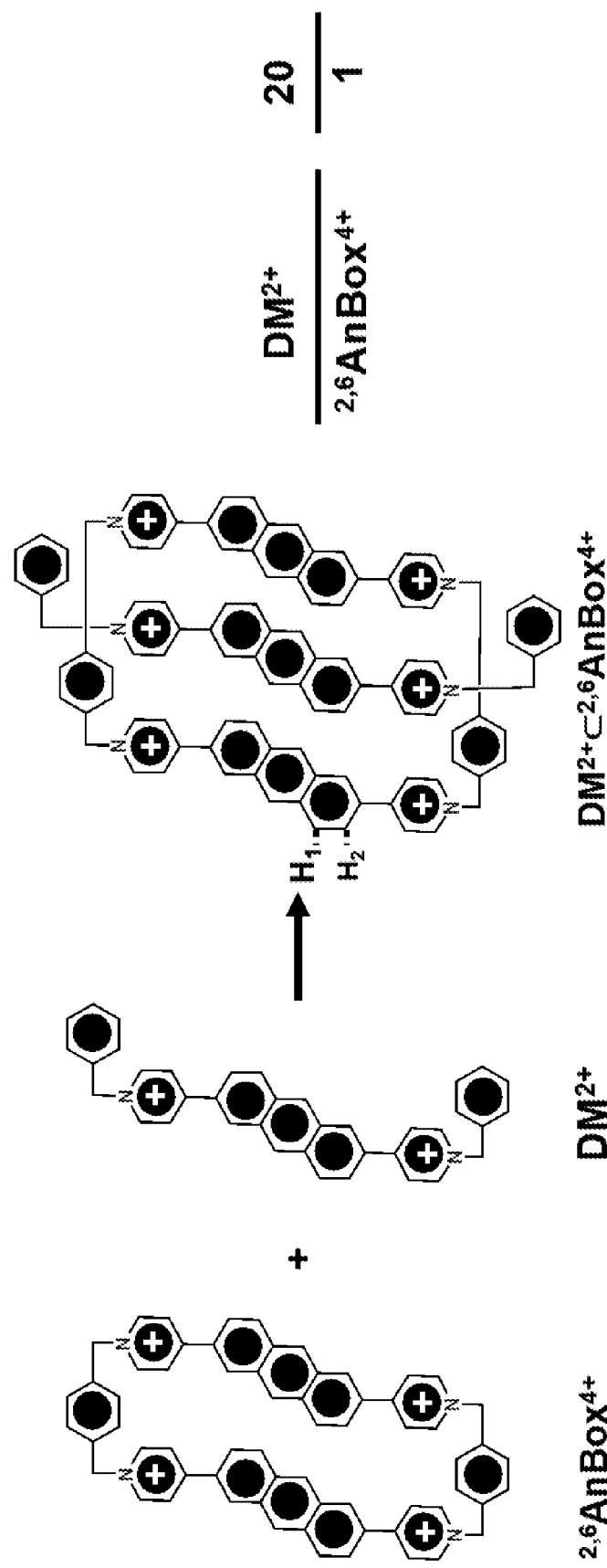

In order to evaluate whether the addition of salt would enhance the synthesis of the rigid $^{2,6}$AnHC.8PF$_6$ homo[2] catenane, we investigated the effects of the addition of tetrabutylammonium hexafluorophosphate (TBAPF$_6$) salt on the formation of the $^{2,6}$AnDB$^{2+}$ ⊂ $^{2,6}$AnBox$^{4+}$ inclusion complex. The $^1$H NMR titration of TBAPF$_6$ into a 1:1 molar mixture of $^{2,6}$AnBox$^{4+}$ and $^{2,6}$AnDB$^{2+}$ in CD$_3$CN reveals (data not shown) a significant broadening of the anthracene proton peaks, hampering a quantitative estimation of the binding constant. Remarkably, the change in color of the solution from yellow to red implies[38] an increase in the strength of the $^{2,6}$AnDB$^{2+}$ ⊂ $^{2,6}$AnBox$^{4+}$ host-guest complex. In order to estimate the magnitude of the association constant between $^{2,6}$AnDB$^{2+}$ and $^{2,6}$AnBox$^{4+}$, we prepared (FIG. 2A-2C, Scheme 8) an anthracene-based dicationic model DM$^{2+}$. In the absence of salt, $^1$H NMR titration of DM$^{2+}$ into $^{2,6}$AnBox$^{4+}$ in CD$_3$CN reveals (FIG. 2A) a weak binding (K$_a$=40 M$^{-1}$) of the DM$^{2+}$ guest inside the $^{2,6}$AnBox$^{4+}$ cavity. Seemingly, the Coulombic repulsion becomes negligible in the presence of a high concentration of salt since the binding constants (K$_a$=540 and 611 M$^{-1}$) of both the monocationic (MM$^+$), and dicationic (DM$^{2+}$) (FIG. 2A) derivatives are similar. Consequently, the efficiency of the catenane synthesis is also found to be sensitive to the addition of TBAPF$_6$. At a salt concentration of 250 mM, the homo[2]catenane $^{2,6}$AnHC.8PF$_6$ was prepared by mixing $^{2,6}$AnBox.4PF$_6$, $^{2,6}$AnDB.2PF$_6$, and $^{2,6}$AnBPY in a 1:2:2 molar ratio in MeCN resulting in an isolated yield of up to 40%. See Scheme 2. The $^1$H NMR spectrum of $^{2,6}$AnHC$^{8+}$ was recorded at room temperature in CD$_3$CN. Only three signals are observed which can be assigned to the pyridinium, methylene, and phenylene protons. All other resonances associated with the anthracene units disappear or are broadened at room temperature. In the temperature dependent 41 NMR spectra (data not shown), the signals for the anthracene protons reappear at low temperature and have been assigned based on 2D ROESY NMR spectroscopic measurements. These experiments confirm the dynamic nature of the homo[2]catenane in which the two mechanically interlocked rings undergo relative co-conformational changes at room temperature. The catenane was also characterized by high-resolution mass spectrometry (HR-MS). A characteristic peak corresponding to [M-3 PF$_6$]$^{3+}$ is present in the mass spectrum (data no shown) at m/z of 823.7819 which compares well with the calculated value for m/z of 823.7814.

Figure 4A:
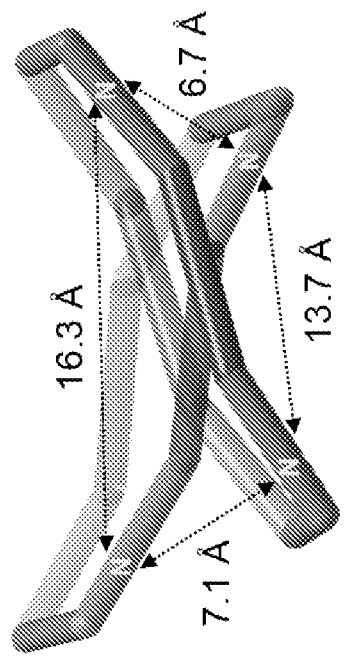
FIGS. 4A-4D shows representations of the solid-state (super)structures of polymorphic $^{2,6}AnHC^{8+}$. Tubular (FIG. 4A) and space-filling (FIG. 4B) representations show the distances associated with $^{2,6}AnHC^{8+}$ obtained from the α-polymorph. Tubular (FIG. 4C) and space-filling (FIG. 4D) representations show the distances associated with $^{2,6}AnHC^{8+}$ obtained from the β-polymorph. All distances are calculated between the N atoms of the pyridinium units.
Figure 4B:
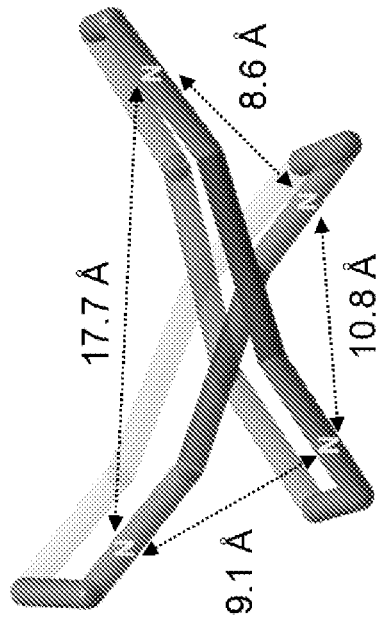
Figure 4C:
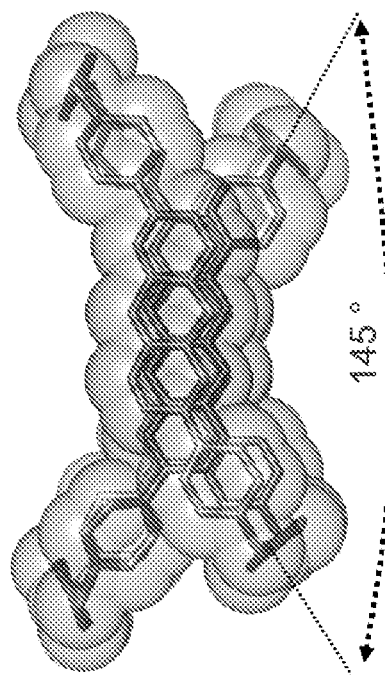
Figure 4D:
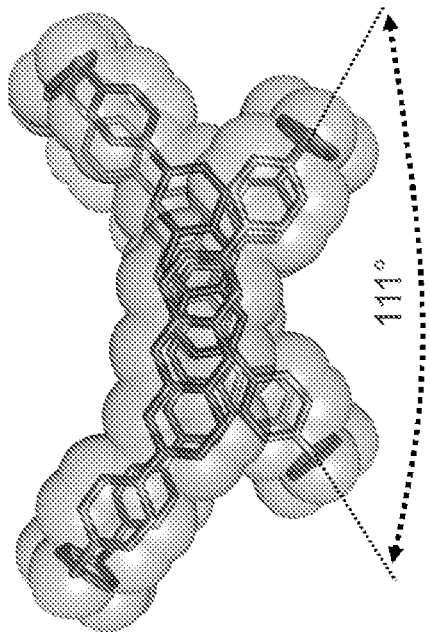

High-quality single crystals of $^{2,6}$AnHC$^{8+}$ were obtained by the slow vapor diffusion of i-Pr$_2$O into an MeCN solution of the $^{2,6}$AnHC.8PF$_6$ during one week. Two crystalline polymorphs of the homo[2]catenane were obtained, depending on the absence or presence of TBAPF$_6$ in the crystallization medium. The distinctions between the α-polymorph (FIG. 3A), obtained without addition of the salt, and the β-polymorph (FIG. 3B), which crystallized from a concentrated salt solution, are subtle and involve differences in the co-conformations in the solid-state structure of the homo[2]catenane. The structure of the α-polymorph displays (FIG. 3A) a regular interplanar face-to-face [π . . . π] distances of 3.4 Å between the four anthracene moieties in the catenane. The collective distances (FIG. 4A) between the positively charged nitrogen atoms in the pyridinium units of the two mechanically interlocked cyclophanes are 8.6/9.1/10.8/17.7 Å, accompanied by a "dihedral" angle (FIG. 4b) of 111°. In the case of the β-polymorph, the solid-state structure of the $^{2,6}$AnHC$^{8+}$ is more symmetrical and displays larger face-to-face [π . . . π] contacts between the anthracene moieties. The interplanar distances between the four anthracene moieties, alternates between 3.3 and 3.6 Å. Notably, the collective distances (FIG. 4C) between the positively charged nitrogen atoms in the pyridinium units of the two mechanically interlocked cyclophanes are 6.7/7.1/13.7/16.3 Å, while the accompany "dihedral" angle (FIG. 4d) is 145°. The discrepancy in the distances between the positively charged nitrogen atoms in the pyridinium units is in agreement with the changes in the chemical shifts observed in the $^1$H NMR spectra recorded in CD$_3$CN during titrations (FIG. 2B) with KPF$_6$. Clearly, the high ionic strength of the solution, not only has a crucial role to play in enhancing the formation of the homo[2]catenane, but also has marked influence in determining the catenane co-conformations, leading to the two polymorphs[39] observed in the solid state.

Optical Studies in Solution

The close proximity of the anthracene units in the mechanically interlocked cyclophanes was expected to give rise to remarkable optical properties distinct from those of the free cyclophanes. We explored the absorption and fluorescence properties of all compounds at high dilution (4×10$^{-7}$ M) to avoid reabsorption processes[40] and aggregation effects.[17] All of the optical parameters are summarized in Tables 1 and 2. Initially, we explored the influence of the pyridine/pyridinium units on the optical properties of both $^{2,6}$AnBox$^{4+}$ and $^{9,10}$AnBox$^{4+}$ cyclophanes. The presence of two pyridinium units within the linker dramatically affect the optical properties of the anthracene moiety. Although $^{2,6}$AnBPY (FIG. 5C) and $^{9,10}$AnBPY display[41] characteristic vibronic peaks associated with the anthracene moiety at 290 and 400 nm, $^{2,6}$AnDB$^{2+}$ and $^{9,10}$AnDB$^{2+}$ display a shift of the band at 290 to 330 nm (FIG. 5A) and the emergence of a new featureless broad band at 450 nm associated with CT from the anthracene moiety to the pyridinium unit. It is noteworthy that phenylene-bridged bipyridyl linkers (ExBIPY) display[35] a single absorption peak at 325 nm in MeCN, while the anthracene moiety leads to the emergence of some push-pull D-A character. Fluorescence spectroscopy reveals that the $^{2,6}$AnBPY and $^{9,10}$AnBPY display[41] a featured emission band at 440 nm characteristic of the vibronic peaks of the anthracene moiety (data not shown).

Figure 5A:
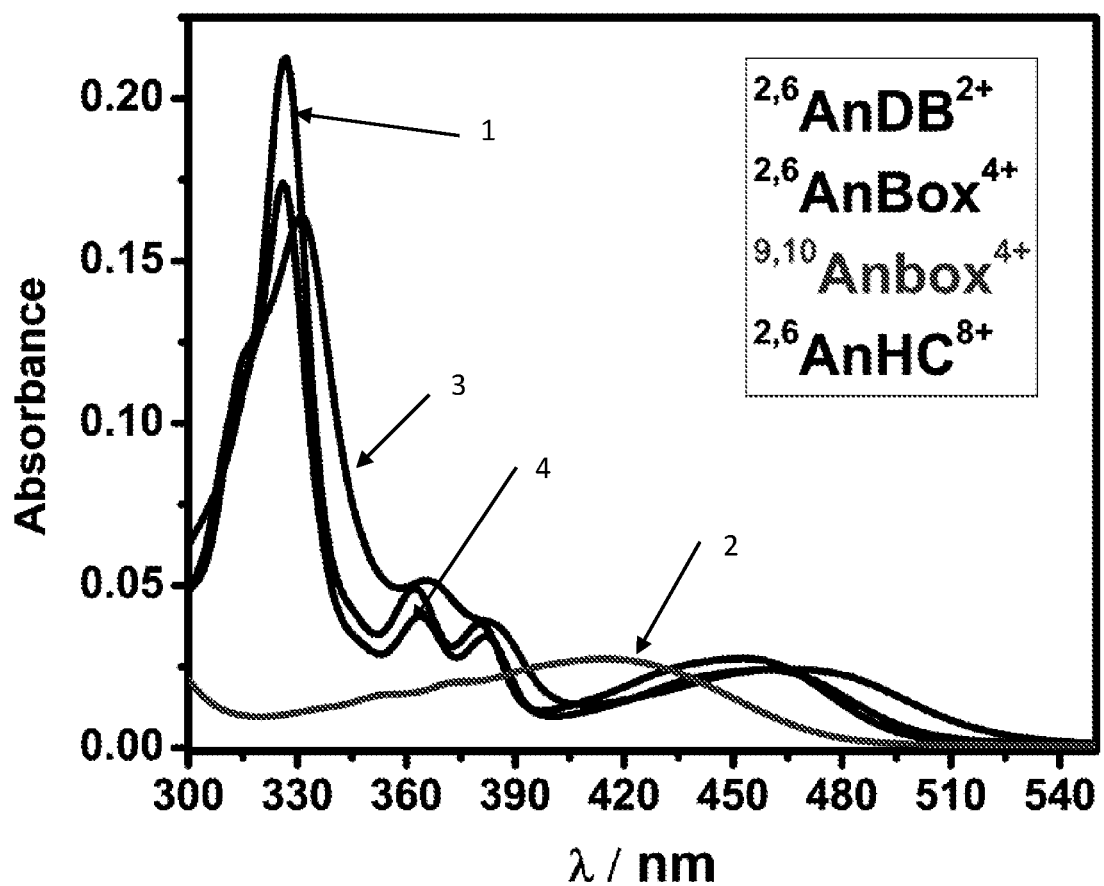
FIGS. 5A-5B.
Figure 5B:
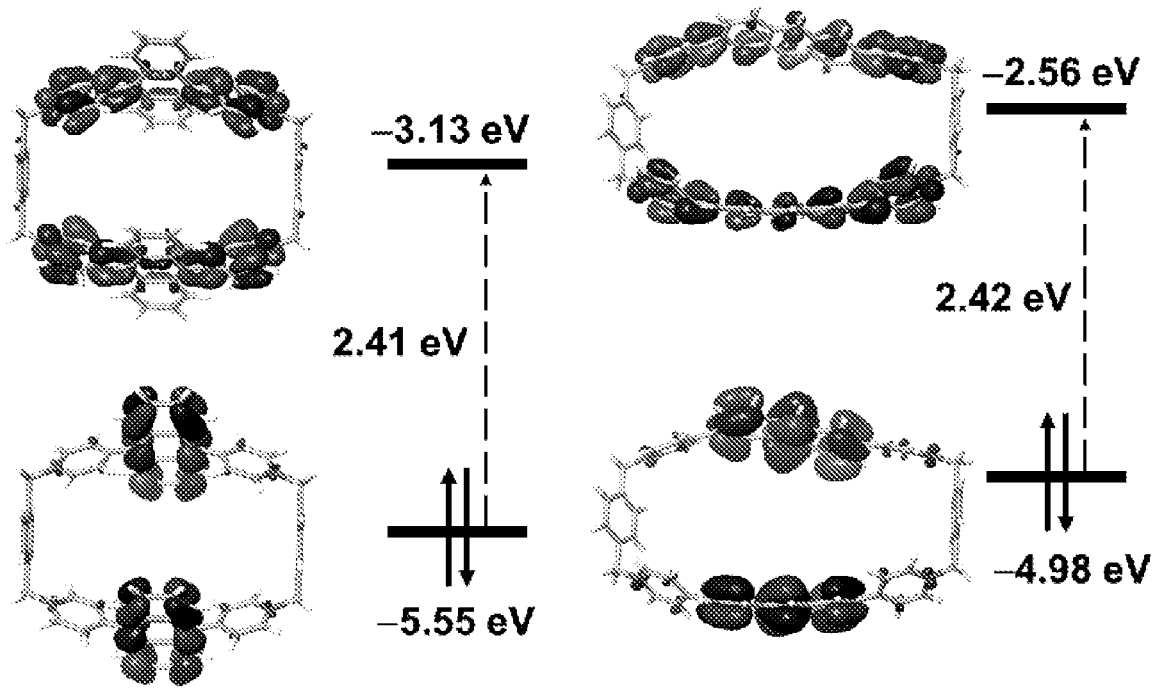
Figure 5C:
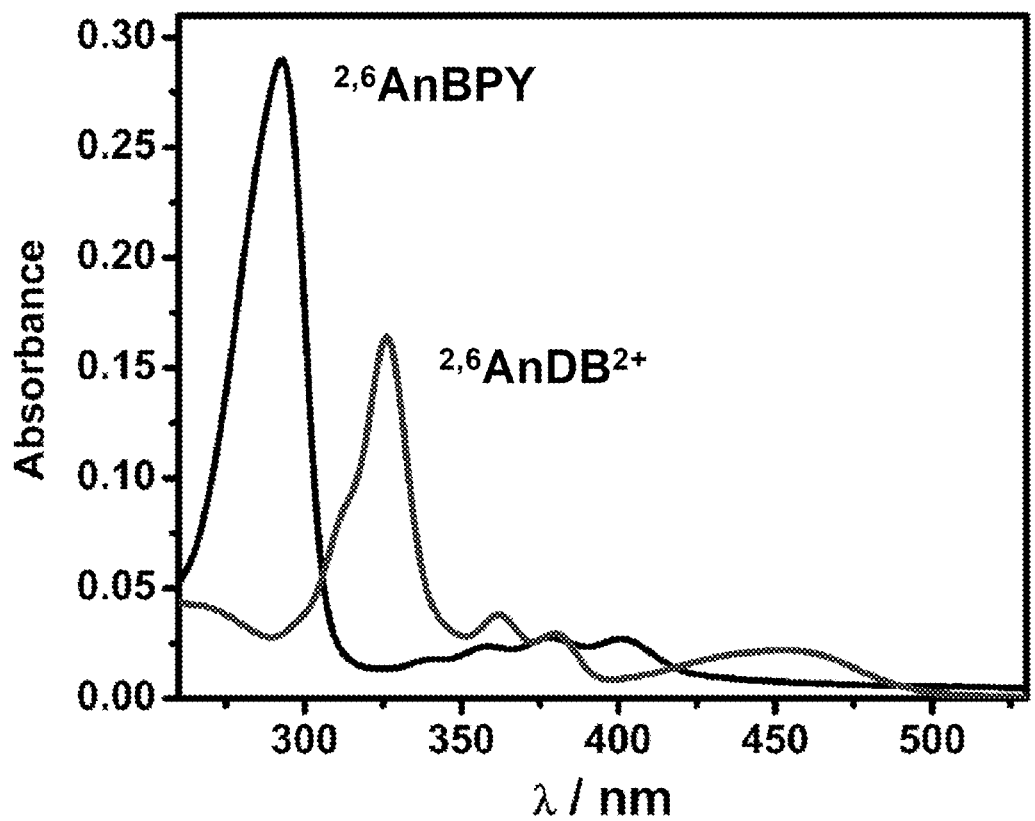
FIG. 5C shows absorption spectra of the $^{2,6}AnBPY$ and $^{2,6}AnDB^{2+}$ in MeCN ($4\times10^{-7}$ M)
Figure 8:
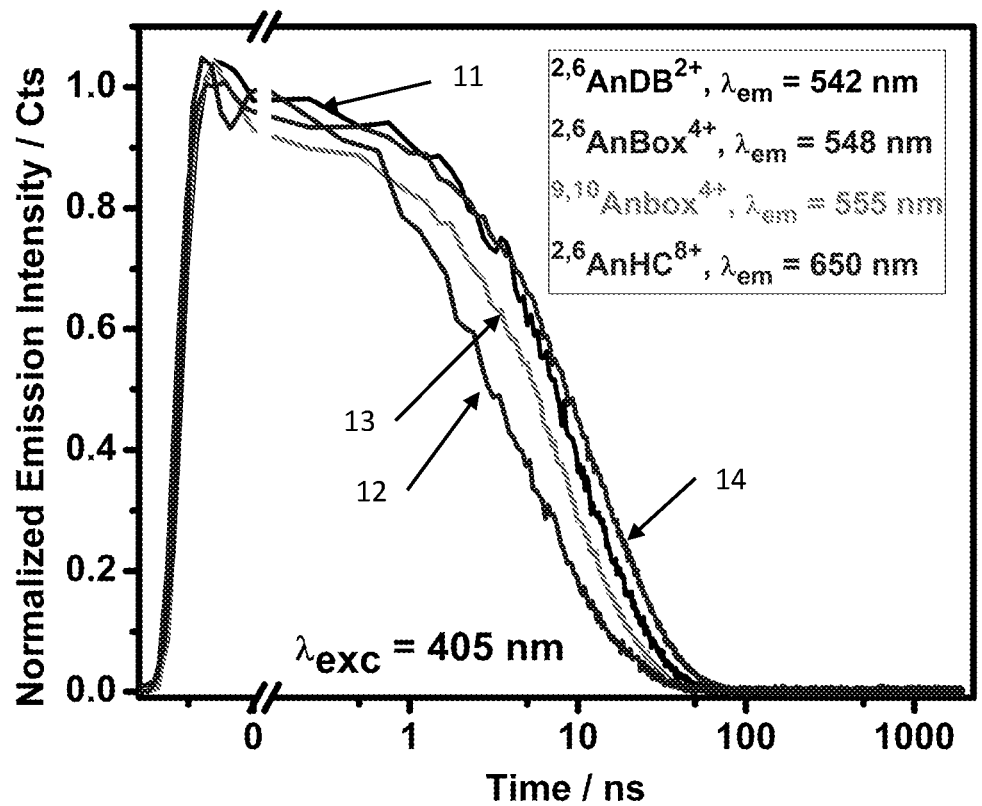
FIG. 8 shows normalized kinetic traces of solutions of $^{2,6}AnDB^{2+}$ (11), $^{9,10}AnBox^{4+}$ (12), $^{2,6}AnBox^{4+}$ (13), and $^{2,6}AnHC^{8+}$ (14) in MeCN upon 405 nm excitation.

The PL spectrum of $^{2,6}$AnDB' has a single broad peak centered at 542 nm with a PL lifetime of 10 ns (FIG. 8), whereas the emission lifetime of anthracene was reported' to be of ~18 ns—indicating the existence of additional pathways of exciton relaxation as a result of the CT character of the $^{2,6}$AnDB$^{2+}$.$^{43}$ In addition, the excitation spectrum at the emission wavelength of 453 nm for $^{2,6}$AnDB$^{2+}$ matches the absorbance spectrum, suggesting that the PL arises from a CT state between the anthracene moieties and pyridinium units. It was anticipated that the photophysical properties of the cyclophanes ($^{2,6}$AnBox$^{4+}$ and $^{9,10}$AnBox$^{4+}$) would be similar to those of the AnDB$^{2+}$ derivatives $^{2,6}$AnDB$^{2+}$ and $^{9,10}$AnDB$^{2+}$ since the distance between the anthracene units is ~7 Å (FIG. 5A). Indeed, a similar CT band is centered at 458 nm while the PL band appears (FIG. 8) at 548 nm, despite the fact that the PL quantum yield decreases to 3.6% and the emission lifetime is significantly shorter (3 ns). Although the UV-Vis and the fluorescence properties of $^{2,6}$AnDB$^{2+}$ and $^{2,6}$AnBox$^{4+}$ are very similar, $^{9,10}$AnDB$^{2+}$ and $^{9,10}$Anbox$^{4+}$ display (data no shown) slight bathochromic shifts for both the absorption and emission spectra, associated' with [π . . . π] interactions between the anthracene moieties. Gas-phase DFT calculations of the frontier orbitals reveal (FIG. 5B) that the HOMO and LUMO orbitals are predominantly localized on the anthracene moieties and the pyridinium units, respectively, with $\Delta E_{HOMO-LUMO}$=2.41 eV.

Figure 6A:
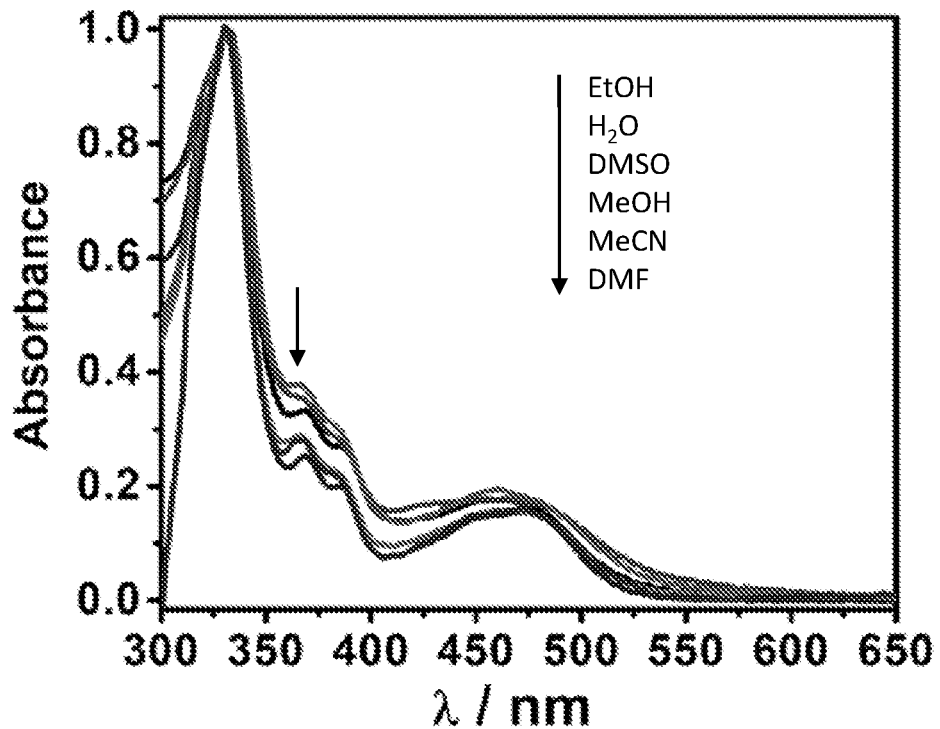
FIGS. 6A-6D show solvatochromic effects in $^{2,6}Anbox^{4+}$ and $^{2,6}AnHC^{8+}$ at a concentration of $4\times10^{-7}$ M.
Figure 6C:
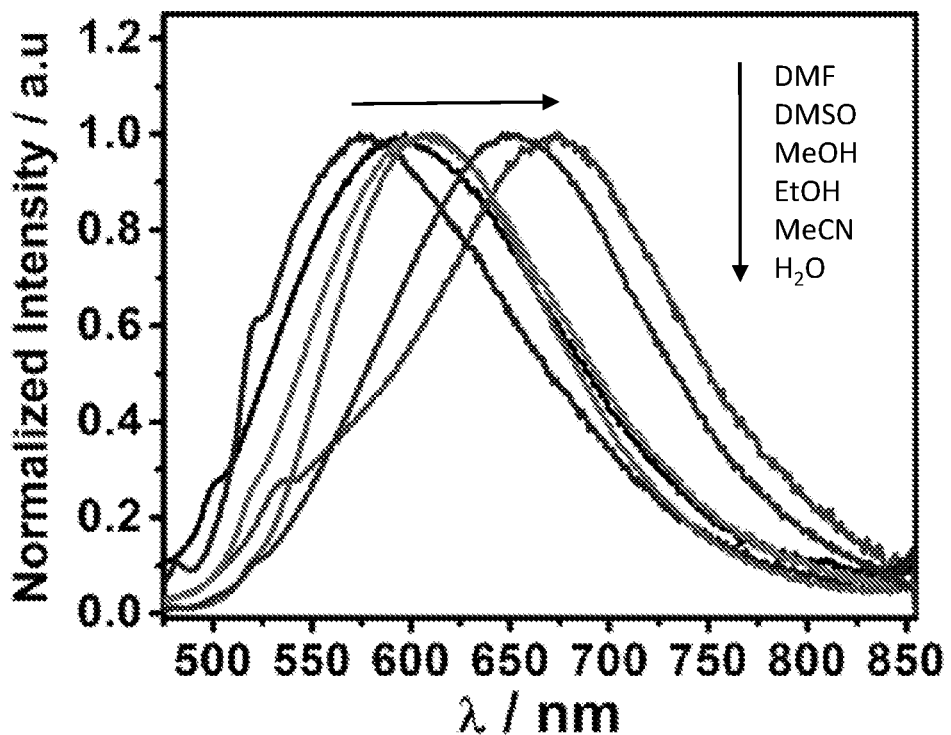

A comparative study of the absorption spectra and luminescence properties of $^{2,6}$AnBox$^{4+}$ (containing two chromophore units separated by a distance >7 Å) and $^{2,6}$AnHC$^{8+}$ (containing four chromophore units separated by a distance >4 Å) was expected to reveal the extent of the electronic interactions between the anthracene moieties and provide information about the role of the mechanical bond in the generation of permanent exciplex fluorescence. For the homo[2]catenane $^{2,6}$AnHC$^{8+}$, we observe a slight bathochromic shift of 10 nm for the CT band in the absorption spectrum (FIG. 5A), undoubtedly associated with CT between the two cyclophanes of the catenane. Both the DFT optimized geometry and X-ray crystallographic analysis of $^{2,6}$AnHC$^{8+}$ show that the anthracene moieties interact with the pyridinium units instead of participating in face-to-face [π . . . π] interactions between the anthracene moieties. The emission spectrum of $^{2,6}$AnHC$^{8+}$ at 4×10$^{-7}$M reveals (FIG. 6C, Table 2) a considerably increased Stokes shift in the PL spectrum, with an emission peak centered at 650 nm, suggesting the formation of an exciplex between the four anthracene moieties in the two mechanically interlocked cyclophanes. The low PL quantum yield (0.5%) and longer PL lifetime (14 ns) suggest (FIG. 8) delayed electron-hole recombination, a hallmark' of exciplex formation in organic molecules.

Figure 9A:
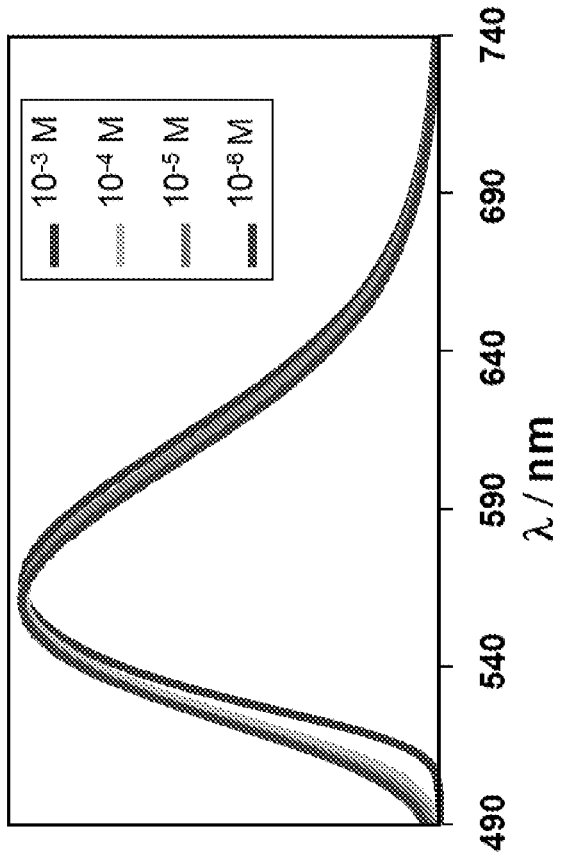
FIGS. 9A-9B shows persistence of the emission in $^{2,6}AnHC^{8+}$ at very low concentrations (MeCN).
Figure 9B:
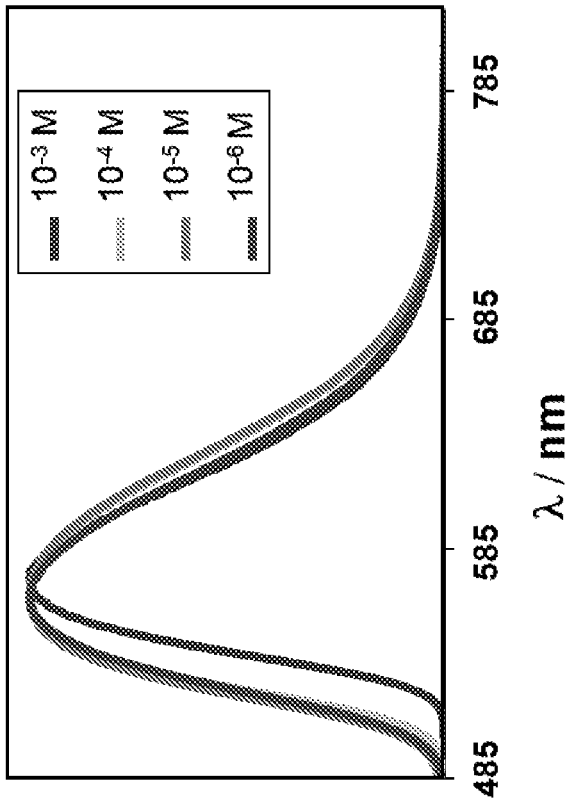
Figure 10A:
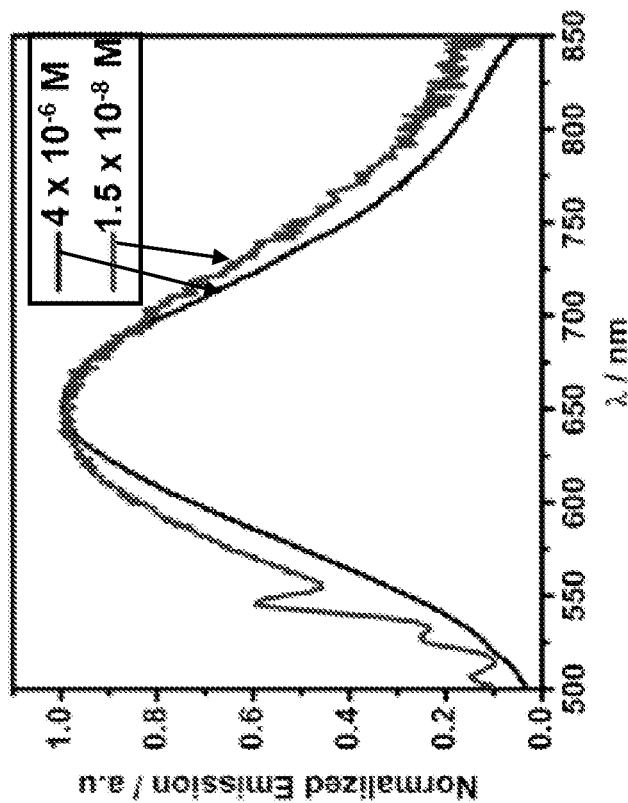
FIGS. 10A-10B.
Figure 10B:
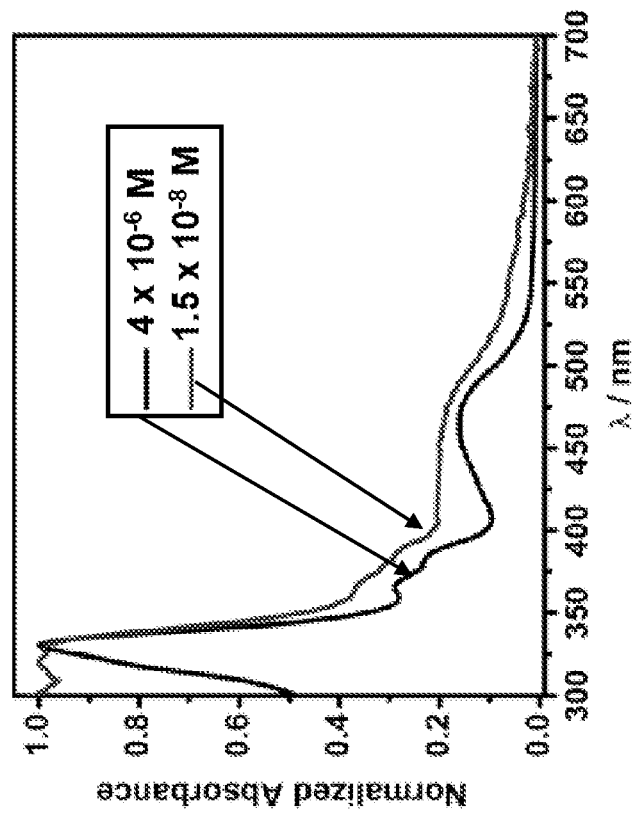

Previous studies revealed[21] that the aggregation of anthracene at high concentrations leads to the emergence of an excimer emission with a ~100 nm bathochromic shift compared to the monomer emission. In the case of homo[2]catenane $^{2,6}$AnHC$^{8+}$, however, the exciplex emission is concentration independent, and it persists (FIG. 9A-9B) at high dilution (10$^{-8}$ M). The concentration-dependence for $^{2,6}$AnDB$^{2+}$ and $^{2,6}$AnBox$^{4+}$ reveals (FIG. 10A-10B) the absence of excimer emission at high concentration as the result of electrostatic repulsion between the cationic anthracene-pyridinium linker. Therefore, the mechanical bond in the homo[2]catenane $^{2,6}$AnHC$^{8+}$is responsible for the persistence of the exciplex emission from $^{2,6}$AnHC$^{8+}$ at low concentrations.

Anthracene-based fluorophores have a strong tendency to aggregate in aqueous media and produce excimer/exciplex emissions at long wavelengths (480-550 nm). We explored the influence of solvent on both the absorption and emission of the homo[2]catenane. UV-Vis absorption spectra collected in different solvents (FIG. 6A) do not display any shift in the CT band at 450 nm, indicative of the absence of aggregates in either aqueous or organic solvents.

Figure 6B:
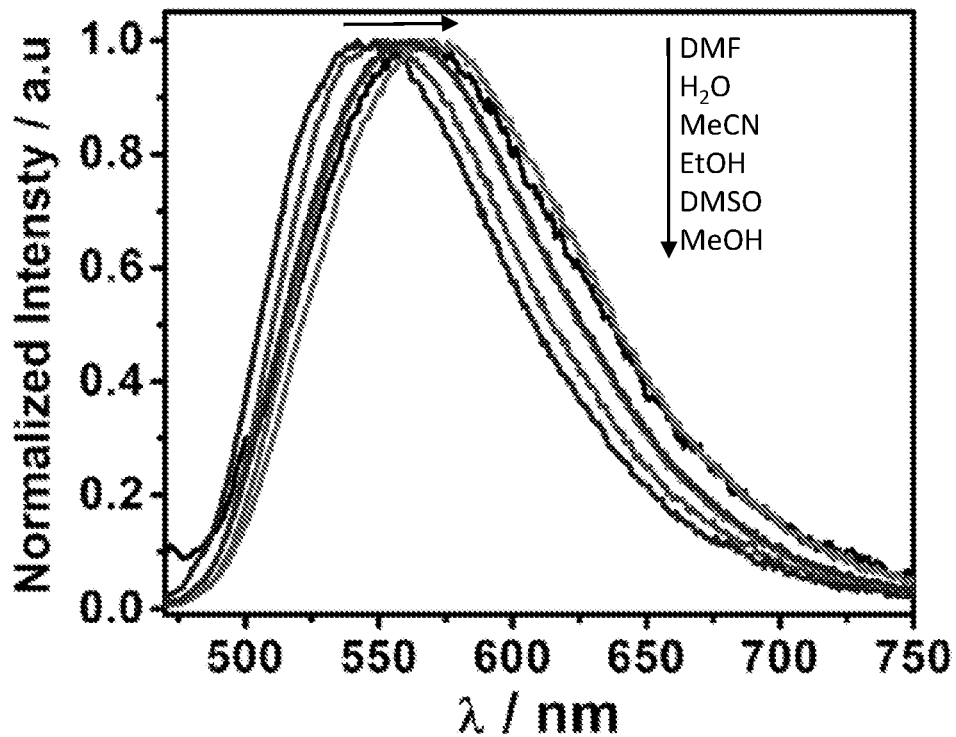
Figure 6D:
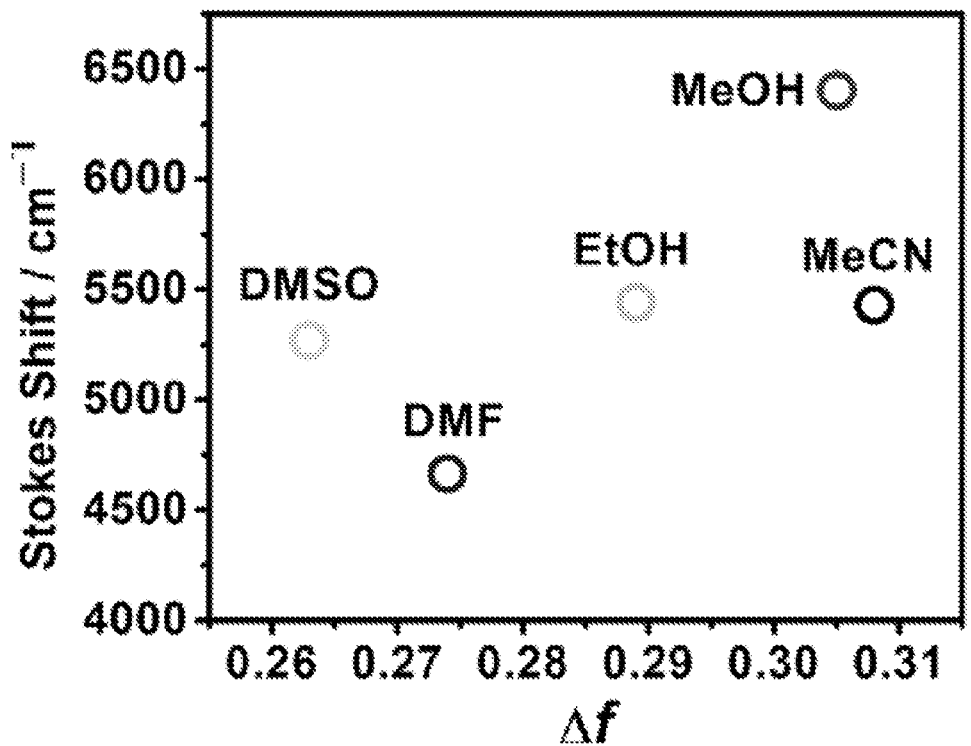
Figure 7A:
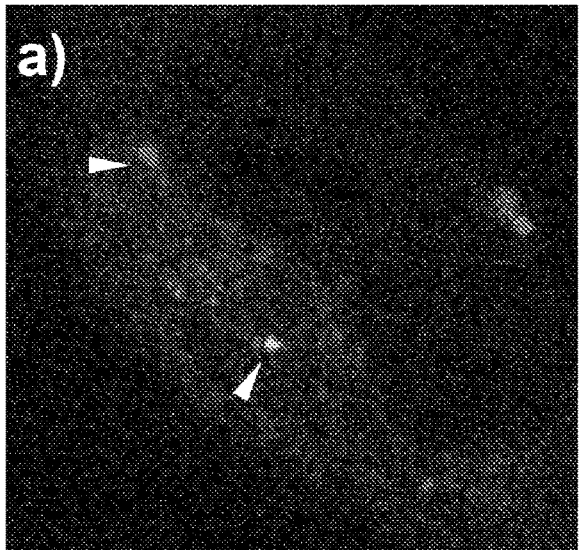
FIGS. 7A-7D show live-cell confocal microscopy images of MIA PaCa-2 prostate cancer cells. Cells were incubated with $^{2,6}AnBox^{4+}\cdot 4Cl$ (20 μM in PBS solution) and $^{2,6}AnHC^{8+}\cdot 8Cl$ (2.5 μM in PBS solution). Composed images of the cells incubated with $^{2,6}AnBox^{4+}\cdot 4Cl$ (FIG. 7A) with green emission (500-575 nm) and $^{2,6}AnHC^{8+}\cdot 8Cl$ (FIG. 7C) with red emission (580-635 nm, shown in magenta). Merged images of the cells incubated with $^{2,6}AnBox^{4+}\cdot 4Cl$ (FIG. 7B) and $^{2,6}AnHC^{8+}\cdot 8Cl$ (FIG. 7D) showing both emission ranges and the transmitted light images.
Figure 7B:
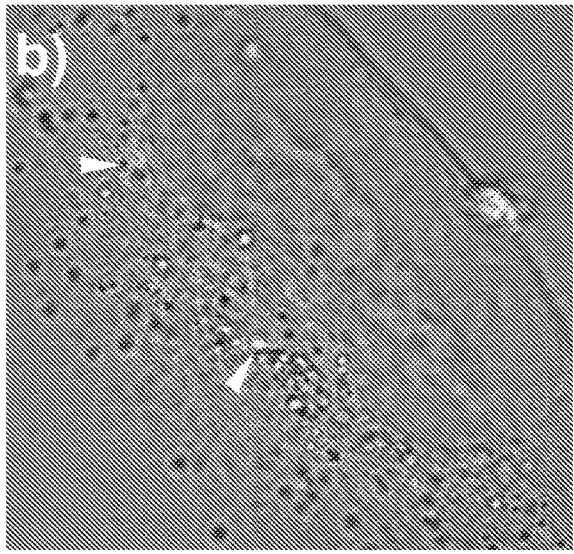
Figure 7C:
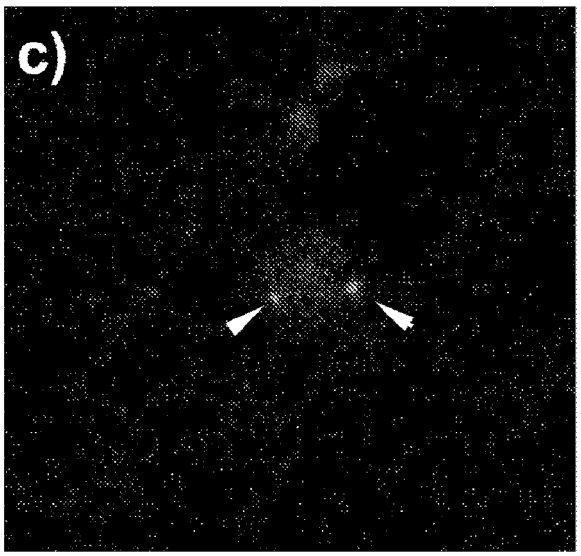
Figure 7D:
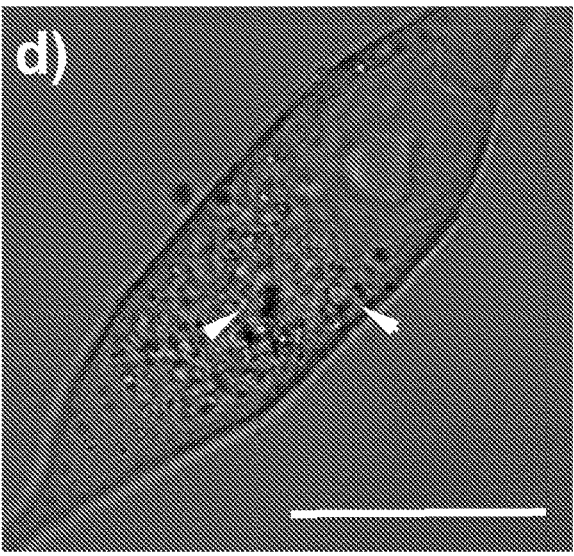

Solvent-induced PL spectroscopic shifts are often interpreted' in terms of the Lippert-Mataga equation, which describes Stokes shifts (6) with respect to the change in the dipole moment of the fluorophore and the dependence of the energy of the dipole on the dielectric constant and refractive index of the solvent. The Lippert-Mataga equation accounts[46] for the general solvent effects but does not consider specific solvent-fluorophore interactions through, for example, hydrogen bonding, or [π . . . π] interactions. Although the emission spectra of $^{2,6}$AnHC$^{8+}$ display strong solvatochromic effects, there is no linear correlation (FIG. 6D) between the solvent polarity and the bathochromic shift. For example (Table 2), in MeCN, the PL is centered at 650 nm, whereas in a more polar solvent such as MeOH, the emission band is centered at 608 nm. In DMF, the emission band is centered at 595 nm ($\delta$=4665 cm$^{-1}$), whereas the PL of $^{2,6}$AnHC$^{8+}$ in water displays the largest bathochromic shift ($\delta$=6924 cm$^{-1}$) with a PL band centered at 675 nm. The influence of the solvent polarity in the PL of $^{2,6}$AnBox$^{4+}$ is less important, with very similar Stokes shifts ($\delta_{DMF}$=3153 cm$^{-1}$, $\delta_{water}$=3284 cm$^{-1}$, FIG. 6B) in DMF and water. The large Stokes shift in water for $^{2,6}$AnHC$^{8+}$ is ascribed instead to the hydrophobic effect, which favors face-to-face [π . . . π] interactions. Previous investigations have shown that organic polar solvents disfavor [π . . . π] interactions, whereas aqueous solutions promote' the aggregation of polyaromatics through face-to-face and/or edge-to-edge [π . . . π] interactions. All these results offer insight into the role of the mechanical bond in the formation, at low concentrations, of permanent exciplex emissions, which could be of interest, for example, in bioimaging.

Cellular Imaging

The live-cell confocal microscopy images for the cyclophane (FIG. 7A-7D) at a 20×10$^{-6}$ M concentration reveal an emission in the green channel (500-575 nm) along with a very weak emission in the red channel (580-635 nm), which was predicted since the cyclophane emits low PL in the red region. No emissions, however, are detected (FIG. 11) at concentrations lower than 10×10$^{-6}$ M. Conversely, in the case of the homo[2]catenane $^{2,6}$AnHC$^{8+}$ at 2.5×10$^{-6}$ M, the images show (FIGS. 7A-7D and FIG. 11) a bright emission in the red channel, although almost no emission is detected in the green channel. We reasoned that the low concentration required to probe the $^{2,6}$AnHC$^{8+}$ within the cells compared to the cyclophane is a result of much better uptake within the cells. This behavior could be attributed to the octacationic nature of the homo[2]catenane and its larger extinction coefficient compared to that of the tetracationic cyclophane. These anthracene moieties in MIMs can be exploited in different biological applications, including (i) as oxygen transporters to cancer cells for photodynamic therapy[49] and (ii) as delivery vehicles[50] for anticancer drugs.

Materials/General Methods/Instrumentation

All reagents were purchased from commercial suppliers (Aldrich or Fisher) and used without further purification. Anthracene derivatives, 9,10-bis(4-pyridyl)anthracene ($^{9,10}$AnBPY) and 2,6-bis(4-pyridyl)anthracene ($^{2,6}$AnBPY) were synthesized following[1,2] reports in the literature. All reactions and manipulations were carried out under a dry N$_2$ atmosphere using standard Schlenk. Thin-layer chromatography (TLC) was performed on silica gel 60 F254 TLC plates (Merck). Column chromatography was carried out using CombiFlash® Automation Systems (Teledyne ISCO) employing both normal phase (RediSep Rf Gold® Normal-Phase Silica) and reverse phase (RediSep Rf Gold® Reversed-phase C18). Absorption spectra were acquired on a Varian Cary 5000 spectrometer in a 2-mm quartz cuvette in MeCN. All the spectra were baseline-corrected with a MeCN blank sample. The photoluminescence spectra of all samples were obtained with a Fluorolog-3 spectrafluorometer (Horiba Jobin Yvon) in a 2-mm quartz cuvette with 3-nm slit width and a front-phase geometry. The time-correlated single photon counting setup is described elsewhere.[3] Nuclear magnetic resonance (NMR) spectra were recorded on a Bruker Avance III 500 and 600 MHz spectrometers, with working frequencies of 500 and 600 MHz ('H NMR) and 125 MHz ($^{13}$C NMR), respectively. Chemical shifts are reported in ppm relative to the signals corresponding to the residual non-deuterated solvents (CD$_3$CN: $\delta$1–1=1.94 ppm and $\delta_C$=1.32 ppm). High-resolution mass spectra (HRMS) were measured on an Agilent 6210 Time of Flight (TOF) LC-MS, using an ESI source, coupled with Agilent 1100 HPLC stack, using direct infusion (0.6 mL min$^{-1}$). The binding constants were determined using this link: website http://supramolecular.org.[4]

Synthetic Protocols and Characterizations of AnDB·2PF$_6$ and AnExBox·4PF$_6$ $^{9,10}$AnDB·2PF$_6$

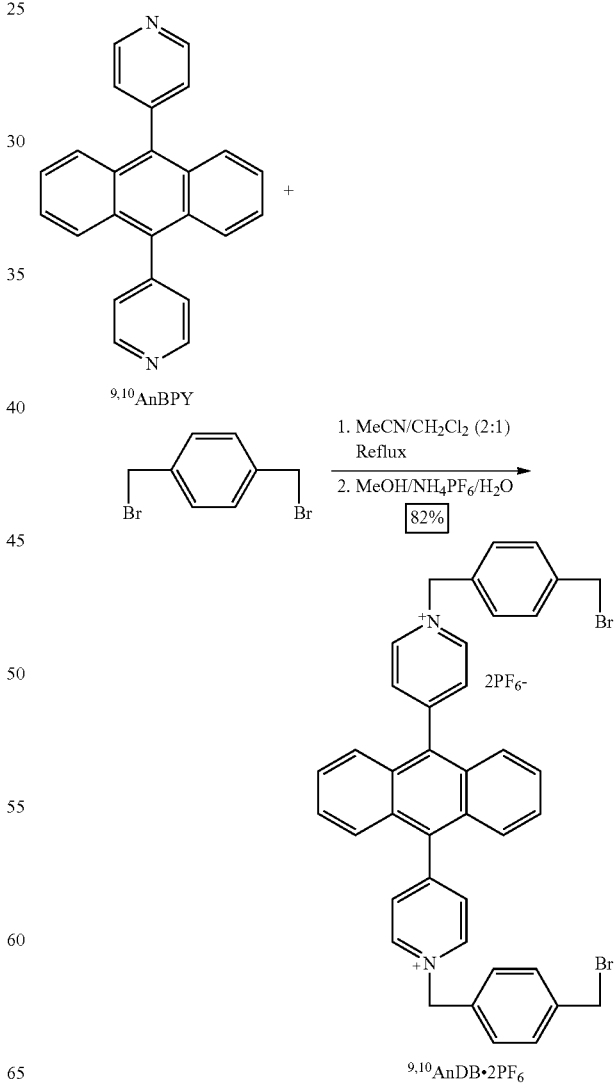

Scheme 2. Synthesis of $^{9,10}$AnDB·2PF$_6$ $^{9,10}$AnDB.2PF$_6$: α,α'-Dibromo-p-xylene (1.6 g, 6 mmol) was dissolved in a dry solvent mixture (CH$_2$Cl$_2$, 20 mL/MeCN, 10 mL), in a 250-mL round-bottomed three-necked flask. The mixture was heated at 60° C. until all of the solid material dissolved. Subsequently, the temperature was raised to 90° C. prior to the addition of five aliquots of a suspension of $^{9,10}$AnBPY (200 mg, 0.6 mmol) in (CH$_2$Cl$_2$, 10 mL: MeCN, 50 mL), slowly over 1 h. The yellow precipitate, indicative of $^{9,10}$AnDB.2Br formation, began to appear after 30 min. The reaction mixture was heated under reflux for 48 h. After cooling to room temperature, the yellow precipitate was collected by filtration and washed with CH$_2$Cl$_2$. The solid was dried in the air for 10 min and dissolved in hot MeOH (~700-900 mL). The addition of NH$_4$PF$_6$ salt (~100-200 mg) and cooling (≤25° C.) H$_2$O (~300 mL), resulted in the precipitation of pure $^{9,10}$AnDB.2PF$_6$ (487 mg, 82%) which was collected by filtration as a yellow solid. $^1$H NMR (500 MHz, CD$_3$CN, ppm): $\delta_H$=8.99 (H$_4$, d, J=6.7 Hz, 4H), 8.17 (H$_5$, J=6.7 Hz, 4H), 7.63 (H$_2$, s, 8H), 7.62-7.54 (H$_6$+H$_7$, m, 8H), 5.89 (H$_3$, s, 4H), 4.66 (H$_1$, s, 4H). $^{13}$C NMR (125 MHz, CD$_3$CN, ppm): $\delta_C$=158.1, 145.8, 141.3, 133.7, 132.2, 131.1, 131.0, 129.3, 128.3, 126.5, 64.9, 33.6. (HRMS-ESI) For $^{9,10}$AnDB.2PF$_6$, Calcd for C$_{40}$H$_{32}$Br$_2$F$_{12}$P$_2$: m/z=350.0542 [M-2PF$_6$]$^{2+}$; 350.0532 [M-2PF$_6$]$^{2+}$.

$^{9,10}$AnBox.4PF$_6$

Scheme 3. Synthesis of $^{9,10}$AnBox•4PF$_6$

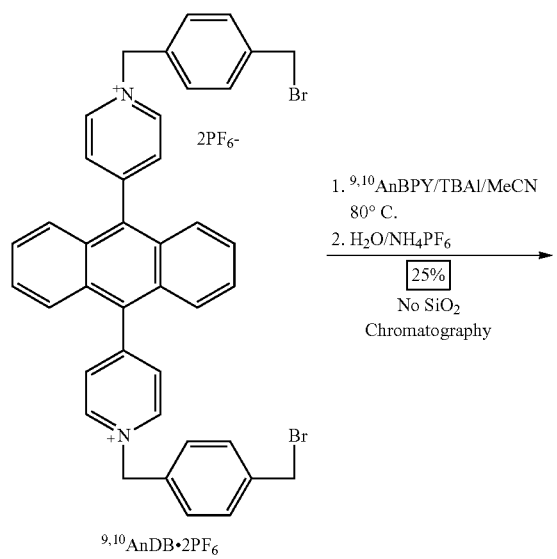

$^{9,10}$AnDB•2PF$_6$

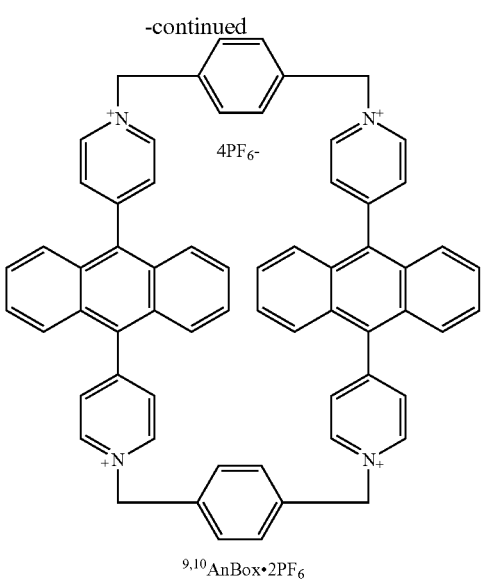

$^{9,10}$AnBox•2PF$_6$ $^{9,10}$AnBox.4PF$_6$: $^{9,10}$AnDB.2PF$_6$ (200 mg, 0.2 mmol), $^{9,10}$AnBPY (67 mg, 0.2 mmol), and tetrabutylammonium iodide (8 mg, 0.04 mmol) were dissolved in a dry solvent mixture (MeCN, 50 mL: CH$_2$Cl$_2$, 10 mL) in a 250-mL round-bottomed three-neck flask. The mixture was heated at 90° C. for 48 h. Subsequently, the addition of concentrated HCl (2-3 mL) led to the precipitation of the crude product, which was washed with CH$_2$Cl$_2$ and dissolved in MeOH. Counterion exchange (NH$_4$PF$_6$) produced the pure $^{9,10}$AnBox.4PF$_6$ cyclophane (58 mg, 25%) which was collected by centrifugation as a yellow solid. $^1$H NMR (500 MHz, CD$_3$CN, ppm): $\delta_H$=9.01 (H$_3$, d, J=6.6 Hz, 8H), 8.01 (H$_4$, J=6.6 Hz, 8H), 7.82 (H$_1$, s, 8H), 7.08 (H$_6$, dd, J=6.8 Hz, 3.2 Hz, 8H), 6.84 (H$_5$, dd, J=6.8 Hz, 3.2 Hz, 8H), 5.94 (H$_2$, s, 4H). $^{13}$C NMR (125 MHz, CD$_3$CN, ppm): $\delta_C$=158.0, 145.3, 137.3, 133.1, 132.3, 131.6, 128.9, 128.0, 126.0, 65.4. (HRMS-ESI) For $^{9,10}$AnBox.4PF$_6$, Calcd for C$_{64}$H$_{48}$F$_{24}$N$_4$P$_4$: m/z=581.4858 [M-2PF$_6$]$^{2+}$; found: 581.4678 [M-2PF$_6$]$^{2+}$.

X-Ray Crystallographic Analysis

Methods: $^{9,10}$AnBox.4PF$_6$ (3.0 mg, 2.4 µmol) was dissolved in MeCN (0.8 mL) and the mixture was passed through a 0.45-µm filter equally into three 1-mL tubes. The tubes were placed together in one 20-mL vial containing iPr$_2$O (~3 mL) and the vial was capped. Slow vapor diffusion of iPr$_2$O into the solution of $^{9,10}$AnBox.4PF$_6$ in MeCN (3.0 mM) over the course of one week yielded yellow single crystals of $^{9,10}$AnBox.4PF$_6$. Data were collected at 100 K on a Bruker Kappa APEX-II CCD Diffractometer equipped with a MoKα microsource with Quazar optics.

Crystal Parameters: [C$_{64}$H$_{48}$N$_4$.(PF$_6$)$_4$].(MeCN)$_2$. Yellow block (0.08×0.06×0.04 mm). Triclinic, P1, a=10.3835(7), b=11.9083(8), c=13.5373(10) Å, α=80.634(4), β=88.346(4), γ=76.950(4)°, V=1608.9(2) Å$^3$, Z=1, T=100(2) K, ρ$_{calc}$=1.584 g cm$^{-3}$, µ=0.24 mm$^{-1}$. Of a total of 7472 reflections which were collected, 5860 were unique (R$_{int}$=0.046). Final R$_1$(F$^2$>2σF$^2$)=0.0044 and wR$_2$=0.0521. The structure was solved by direct methods and expanded using Fourier techniques. Disordered PF$_6^-$ ions were refined with similarity restraints on P-F and F-F distances to keep geometries reasonable, as well as with rigid bond and similarity restraints to keep displacement parameters reasonable. CCDC Number: 1983956.

2,6AnDB·2PF6

Scheme 4. Synthesis of 2,6AnDB·2PF6

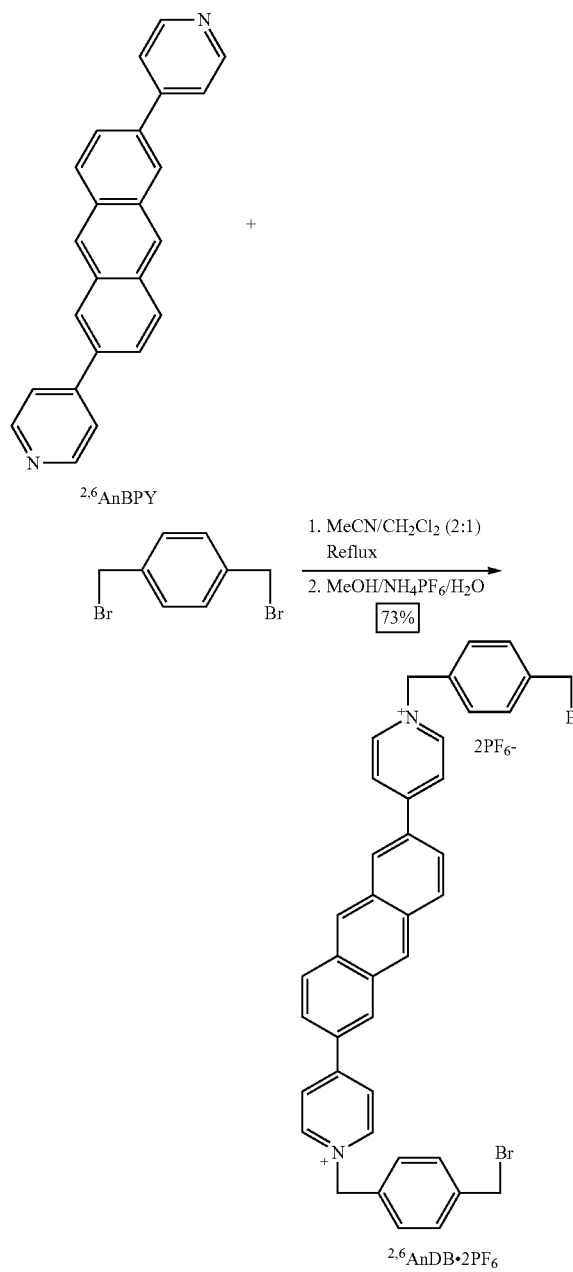

2,6AnDB·2PF6: a,a'-Dibromo-p-xylene (1.6 g, 6 mmol) was dissolved in a dry solvent mixture (CH2Cl2, 20 mL: MeCN, 10 mL), in a 250-mL round-bottomed three-necked flask. The mixture was heated at 60° C. until all of the solid material dissolved. Subsequently, the temperature was raised to 90° C. prior to the addition of five aliquots of a suspension of 9,10AnBPY (200 mg, 0.6 mmol) in (CH2Cl2, 10 mL: MeCN, 50 mL), slowly during 1 h. The yellow precipitate, indicative of 2,6AnDB·2Br formation, began to appear after 30 min. The reaction mixture was heated under reflux for 48 h. After cooling to room temperature, the yellow precipitate was collected by filtration and washed with CH2Cl2. The solid was dried in the air for 10 min and dissolved in hot MeOH (—700-900 mL). The addition of NH4PF6 salt (—100-200 mg) and cooling (≤25° C.) H2O (~300 mL), resulted in the precipitation of pure 9,10AnDB·2PF6 (434 mg, 73%) which was collected by filtration as an orange solid. $^1$H NMR (500 MHz, CD3CN, ppm): $\delta_H$=8.91–8.69 ($H_{5+}H_{7+}H_9$, m, 8H), 8.46 ($H_6$, d, J=7.0 Hz, 4H), 8.37 ($H_{10}$, d, J=9.0 Hz, 2H), 8.00 ($H_8$, dd, J=8.9 Hz, 2.0 Hz, 2H), 7.56 ($H_3$, d, J=8.3 Hz, 4H), 7.48 ($H_2$, d, J=8.3 Hz, 4H), 5.73 ($H_4$, s, 4H), 4.62 ($H_1$, s, 4H). $^{13}$C NMR (125 MHz, CD3CN, ppm): $\delta_C$=157.3, 145.4, 141.1, 134.3, 132.8, 131.5, 131.4, 131.1, 130.4, 129.9, 126.6, 124.8, 64.2, 33.6. (HRMS-ESI) For 2,6AnDB·2PF6, Calcd for $C_{40}H_{32}Br_2F_{12}N_2P_2$: m/z=350.0536 [M-2PF6]$^{2+}$; 350.0538 [M-2PF6]$^{2+}$. 2,6AnExBox·4PF6

Scheme 5. Synthesis of 2,6AnBox·4PF6

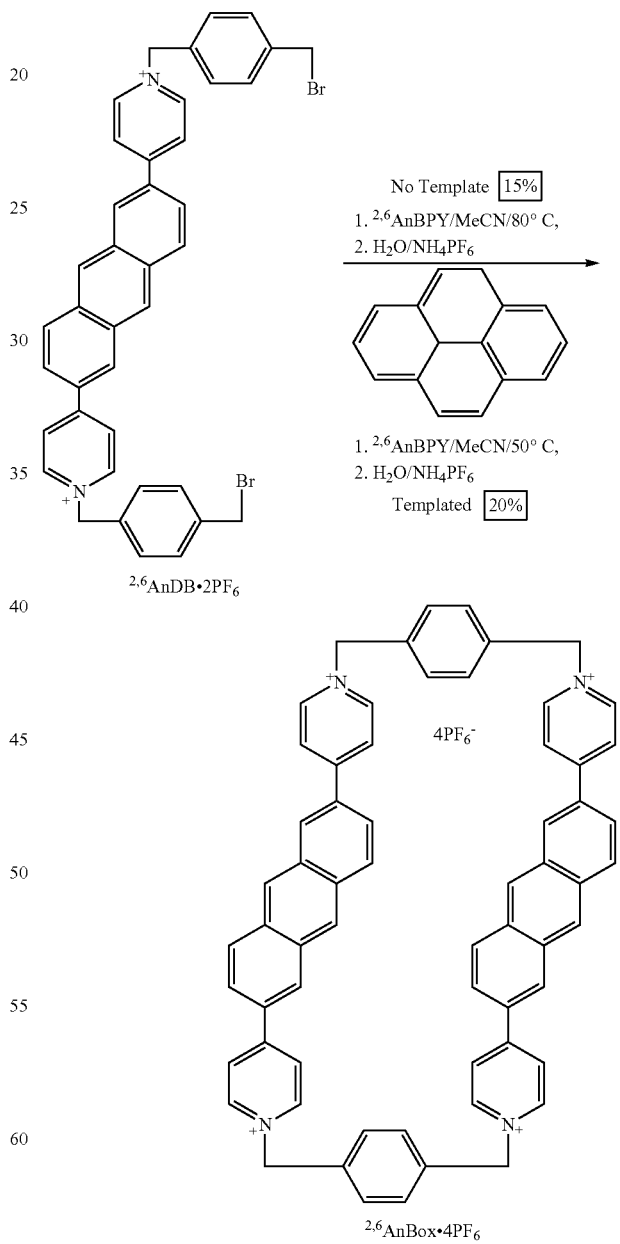

2,6AnBox·4PF6: Two synthetic routes were employed (Scheme S4) to prepare the tetracationic cyclophane. The first route consisted of adding $^{2,6}$AnDB.2PF$_6$ (200 mg, 0.2 mmol), $^{2,6}$AnBPY (67 mg, 0.2 mmol), and tetrabutylammonium iodide (15 mg, 0.04 mmol) in a dry solvent mixture (MeCN, 50 mL: CH$_2$Cl$_2$, 10 mL), in a 250 mL round-bottomed three-necked flask. The solution mixture was heated at 90° C. for 48 h. Subsequently, the addition of concentrated HCl (2-3 mL) led to the precipitation of the crude product, which was washed with CH$_2$Cl$_2$ and dissolved in MeOH. Finally, pure $^{2,6}$AnBox.4PF$_6$ was obtained after running a reverse-phase chromatography column using (C$_{18}$: H$_2$O/MeCN 0.1% TFA 0-100%) followed by anion exchange from TFA$^-$ to PF$_6^-$ in 15% yield as a yellow solid (44 mg).

The second synthetic route consisted of adding $^{2,6}$AnDB.2PF$_6$ (200 mg, 0.2 mmol), $^{2,6}$AnBPY (67 mg, 0.2 mmol), and the template pyrene (106 mg, 0.5 mmol) to dry solvent mixture (MeCN, 50 mL: CH$_2$Cl$_2$, 10 mL). The reaction mixture was stirred at 90° C. for 30 min until a clear solution was obtained. Subsequently, the solution was cooled down to 50° C. and stirred for 5 days. The reaction was stopped by adding concentrated HCl (2-3 mL), which led to the precipitation of the crude product. The precipitate was washed with CH$_2$Cl$_2$ and dissolved in MeOH. The product was precipitated from the MeOH solution by adding NH$_4$PF$_6$ (~50-100 mg) before being subjected to column chromatography using reversed-phase flash chromatography (C$_{18}$: water/MeCN 0.1% TFA 0-100%). Anion exchange from TFA$^-$ to PF$_6^-$ was effected by treating the aqueous fractions with an excess of NH$_4$PF$_6$, resulting in a yellow precipitate which was collected by centrifugation and washed with H$_2$O several times before being dried in vacuo to yield the pure product (58 mg, 20%) as a yellow solid. $^1$H NMR (500 MHz, CD$_3$CN, ppm): 8.78 (H$_3$, d, J=7.0 Hz, 8H), 8.53 (H$_5$+H$_6$, s, 8H), 8.28 (H$_4$, d, J=7.1 Hz, 8H), 8.13 (H$_8$, d, J=9.0 Hz, 4H), 7.82 (H$_7$, dd, J=8.9 Hz, 1.9 Hz, 4H), 7.65 (H$_1$, s, 8H), 5.69 (H$_2$, s, 8H). $^{13}$C NMR (125 MHz, CD$_3$CN, ppm): $\delta_C$=156.6, 144.9, 137.1, 133.3, 133.1, 132.0, 131.3, 131.1, 129.8, 126.3, 124.3, 64.6. (HRMS-ESI) For $^{2,6}$AnBox.4PF$_6$, Calcd for C$_{64}$H$_{48}$F$_{24}$N$_4$P$_4$: m/z=581.159 [M-2PF$_6$]$^{2+}$; found: 581.158 [M 2P F$_6$]$^{2+}$.

X-Ray Crystallographic Analysis

Methods: $^{2,6}$AnBox.4PF$_6$ (3.0 mg, 2.4 µmol) was dissolved in MeCN (0.8 mL) and the mixture was passed through a 0.45 µm filter equally into three 1-mL tubes. The tubes were placed together in one 20-mL vial containing iPr$_2$O (~3 mL) and the vial was capped. Slow vapor diffusion of iPr$_2$O into the solution of $^{2,6}$AnBox.4PF$_6$ in MeCN (3.0 mM) over the course of one week yielded yellow single crystals of $^{2,6}$AnBox.4PF$_6$. Data were collected at 100 K on a Bruker Kappa APEX CCD Diffractometer equipped with a CuKα microsource with Quazar optics.

Crystal Parameters:

[C$_{64}$H$_{48}$N$_4$.(PF$_6$)$_4$].(MeCN)$_2$. Yellow plate (0.33×0.15× 0.06 mm). orthorhombic, Ccce, a=12.0098(9), b=34.634(3), c=39.679(3) Å, α=90.000, β=90.000, γ=90.000°, V=16504 (2) Å$^3$, Z=8, T=100(2) K, $\rho_{calc}$=1.556 g·cm$^{-3}$, µ=1.68 mm$^{-1}$. Of a total of 5339 reflections which were collected, 5339 were unique (R$_{int}$=0.051). Final R$_1$(F$^2$>2σF$^2$)=0.075 and wR$_2$=0.0684. Using Olex2,$^6$ the structure was solved with the ShelXT$^7$ structure solution program using Intrinsic Phasing and refined with the ShelXL$^8$ refinement package using Least Squares minimisation. Distance restraints were imposed on the disordered PF6 anion. The enhanced rigid-bond restraint (SHELX keyword RIGU) was also applied on the disordered PF6 anion. (Acta Cryst. A68 (2012) 448-451). The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=4511.5 Å$^3$ [27.5%] Total electron count/cell=986.0 CCDC Number: 1983957.

Anthracene ⊂$^{2,6}$AnBox.4PF$_6$ 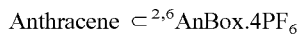

Methods: $^{2,6}$AnBox.4PF$_6$ (3.0 mg, 2.4 µmol) was dissolved in MeCN (0.8 mL). Solid anthracene (0.52 mg, 2.9 µmol) was added to a solution of $^{2,6}$AnBox.4PF$_6$ and, after it had dissolved, the mixture was passed through a 0.45-µm filter equally into three 1-mL tubes. Slow vapor diffusion of iPr$_2$O (~3 mL) into the solution of anthracene and $^{2,6}$AnBox.4PF$_6$ in MeCN over the period of 5 days yielded red single crystals of Anthracene c$^{2,6}$AnBox.4PF$_6$. Data were collected at 100 K on a Bruker Kappa APEX2 CCD Diffractometer equipped with a CuKα microsource with MX optics.

Crystal Parameters: [C$_{64}$H$_{48}$N$_4$·C$_{14}$H$_{10}$·(PF$_6$)$_4$]. Red block (0.12×0.06×0.05 mm). Triclinic, P1, a=7.2668(16), b=12.680(3), c=20.209(7) Å, α=80.52(3), β=84.99(2), γ=87.23° (2), V=1828.6(9) Å$^3$, Z=1, T=100(2) K, $\rho_{calc}$=1.565 g·cm$^{-3}$, µ=1.97 mm$^{-1}$. Of a total of 4880 reflections which were collected, 2225 were unique (R$_{int}$=0.129). Final R$_1$(F$^2$>2σF$^2$)=0.146 and wR$_2$=0.374. The (super)structure was solved by direct methods and expanded using Fourier techniques. Disordered PF$_6^-$ molecules were refined with similarity restraints on P—F and F—F distances to keep geometries reasonable, as well as with rigid bond and similarity restraints to keep displacement parameters reasonable. CCDC Number: 1983955.

$^{2,6}$AnHC.8PF$_6$

Scheme 6. Syntheis of $^{2,6}$AnHC•PF$_6$ 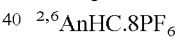

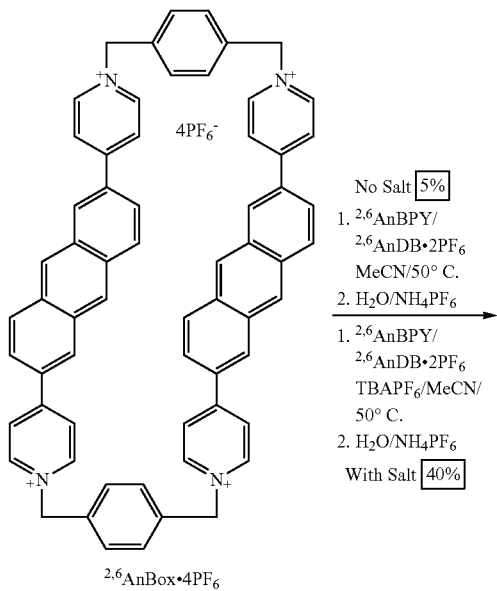

$^{2,6}$AnBox•4PF$_6$

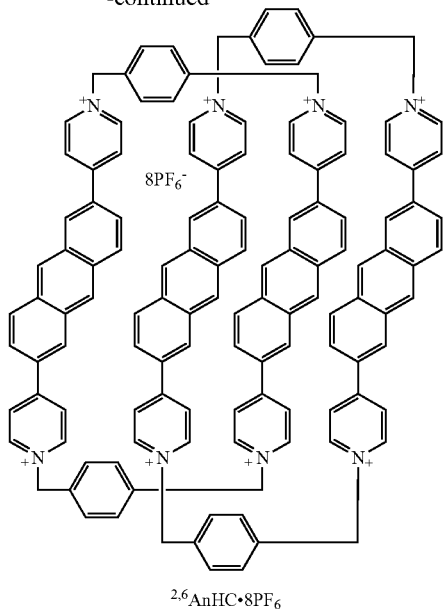

2,6AnHC·8PF6

2,6AnHC.8PF6:

Protocol 1: 2,6AnBox.4PF6 (20 mg, 0.014 mmol), 2,6AnDB.2PF6 (28 mg, 0.028 mmol), 2,6AnBPY (10 mg, 0.028 mmol) were added to dry MeCN (4 mL). The reaction mixture was heated for 30 min at 90° C. until all the reactants had dissolved. Subsequently, the clear solution was stirred at 50° C. After 12 h, the reaction mixture was cooled down to room temperature. The precipitate was collected by filtration and then dissolved in MeOH. Counterion exchange was accomplished by the addition of NH4PF6 (—50-100 mg), resulting in the precipitation of the crude product. The final product was purified using preparative TLC chromatography (Me2CO 0.2% NH4PF6), followed by recrystallization in MeCN, on slow vapor diffusion of iPrO2, yielding pure 2,6AnHC.8PF6 (16 mg, 5%) as red crystals.

Protocol 2: 2,6AnBox.4PF6 (20 mg, 0.014 mmol), 2,6AnDB.2PF6 (28 mg, 0.028 mmol), 2,6AnBPY (10 mg, 0.028 mmol), and an excess of tetrabutylammonium hexafluorophosphate (160 mg, 0.98 mmol) were added to dry MeCN (4 mL). The reaction mixture was heated for 30 min at 90° C. until all the reactants had dissolved. Subsequently, the clear solution was maintained at 50° C. After 2 h, red crystals appeared. After 12 h the reaction mixture was cooled down to room temperature. The red crystals were collected by filtration and then dissolved in MeOH. Counterion exchange was accomplished by the addition of NH4PF6 (~50-100 mg), resulting the precipitation of the crude product. The final product was purified using preparative TLC chromatography (Me2CO 0.2% NH4PF6), followed by recrystallization in MeCN, on slow vapor diffusion of iPrO2, yielding pure 2,6AnHC.8PF6 (16 mg, 40%) as red crystals. $^1$H NMR (600 MHz, CD3CN, ppm): $\delta_H$ 8.86 (H$_\alpha$, d, J=6.1 Hz), 8.76 (H$_{\alpha'}$, d, J=6.1 Hz), 8.00-7.95 (H$_\beta$/H$_{\beta'}$, 16H), 7.91 (H$_{C6H4}$, m, 12H), 7.85 (H'$_{An}$, br, 4H), 7.64 (H$_{An}$, s, 12H), 7.52 (H$_{C6H4}$, s, 4H), 7.31-7.13 (H'$_{An}$, m, J=87.0 Hz, 8H), 6.74 (H$_{An}$, s, 4H), 5.85 (H$_{CH2}$, s, 8H), 5.76 (d, J=14.0 Hz, 4H), 5.69 (d, J=14.3 Hz, 4H), 5.48 (H'$_{An}$, br, 4H). (HRMS-ESI) For 2,6AnHC.8PF6, Calcd for C128H96F48N8P8: m/z=823.535 [M-3PF6]$^{3+}$; found: 823.5341 [M-PF6]$^{3+}$.

X-Ray Crystallographic Analysis

Methods: 2,6AnHC.8PF6 (3.0 mg, 2.4 µmol) was dissolved in MeCN (0.8 mL) and the mixture was passed through a 0.45-µm filter equally into three 1-mL tubes. The tubes were placed together in a 20 mL vial containing iPr2O (~3 mL) and the vial was capped. Slow vapor diffusion of iPr2O into the solution of 2,6AnHC.8PF6 into MeCN (3.0 mM) over the course of one week yielded yellow single crystals of 2,6AnHC.8PF6. Data were collected at 100 K on a Bruker Kappa APEX CCD Diffractometer equipped with a CuKα microsource with Quazar™ optics.

Crystal Parameters: [C128H96N8.(PF6)8].(MeCN)2. Red block (0.15×0.14×0.10 mm). Monoclinic, C2/c, a=41.838, b=12.659, c=29.003 Å, α=90.000, β=94.520, γ=90.000°, V=15313.01 Å$^3$, Z=8, T=100 K, $\rho_{calc}$=1.236 g·cm$^{-3}$, µ=0.20 mm$^{-1}$. Of a total of 11376 reflections which were collected, 7806 were unique (R$_{int}$=0.044). Final R$_1$(F$^2$>2σF$^2$)=0.0122 and wR$_2$=0.1234. Using Olex2,$^6$ the structure was solved with the ShelXT$^7$ structure solution program using Intrinsic Phasing and refined with the ShelXL$^8$ refinement package using Least Squares minimisation. Distance restraints were imposed on the disordered PF6 anion. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=2108.0 Å$^3$ [13.8%] Total electron count/cell=419.6. CCDC Number: 1983952.

Methods: 2,6AnHC.8PF6 (3.0 mg, 2.4 µmol) was dissolved in MeCN (1 mL) in the presence of (50 mM) of TBAPF6. Slow evaporation of the mixture over the course of 2 days yielded red single crystals of 2,6AnHC.8PF6. Data were collected at 100 K on a Bruker Kappa APEX CCD Diffractometer equipped with a CuKα microsource with Quazar optics.

Crystal Parameters: [C128H96N8.(PF6)8].(MeCN)4. Red plate (0.48×0.18×0.02 mm). Orthorhombic, P222$_1$, a=11.933, b=14.180, c=42.533 Å, α=90.000, β=90.000, γ=90.000°, V=7197.2 Å$^3$, Z=4, T=100 K, $\rho_{calc}$=1.360 g·cm$^{-3}$, µ=1.90 mm$^{-1}$. Of a total of 11178 reflections which were collected, 7529 were unique (R$_{int}$=0.090). Final R$_1$(F$^2$>2σF$^2$)=0.197 and wR$_2$=0.484. Using Olex2,$^6$ the structure was solved with the ShelXT$^7$ structure solution program using Intrinsic Phasing and refined with the ShelXL$^8$ refinement package using Least Squares minimisation. Distance restraints were imposed on the PF6 anions and the C58-C63 ring. Rigid bond restraints on similar amplitudes separated by less than 1.7 Ang. were imposed globally. A racemic twin was found. The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=1311.4 Å$^3$ [18.2%] Total electron count/cell=257.3. CCDC Number: 1983954.

MM·PF₆

Scheme 7. Syntheis of MM·PF₆

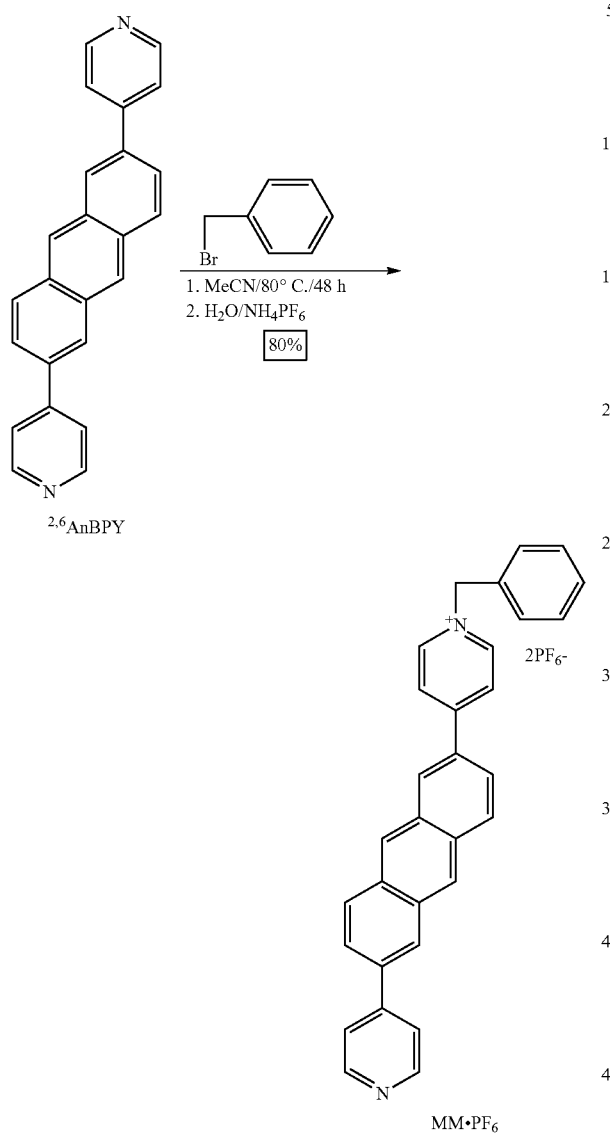

DM·2PF₆

Scheme S8. Synthesis of DM·2PF₆
Scheme 8. Synthesis of DM·2PF₆.ₐ

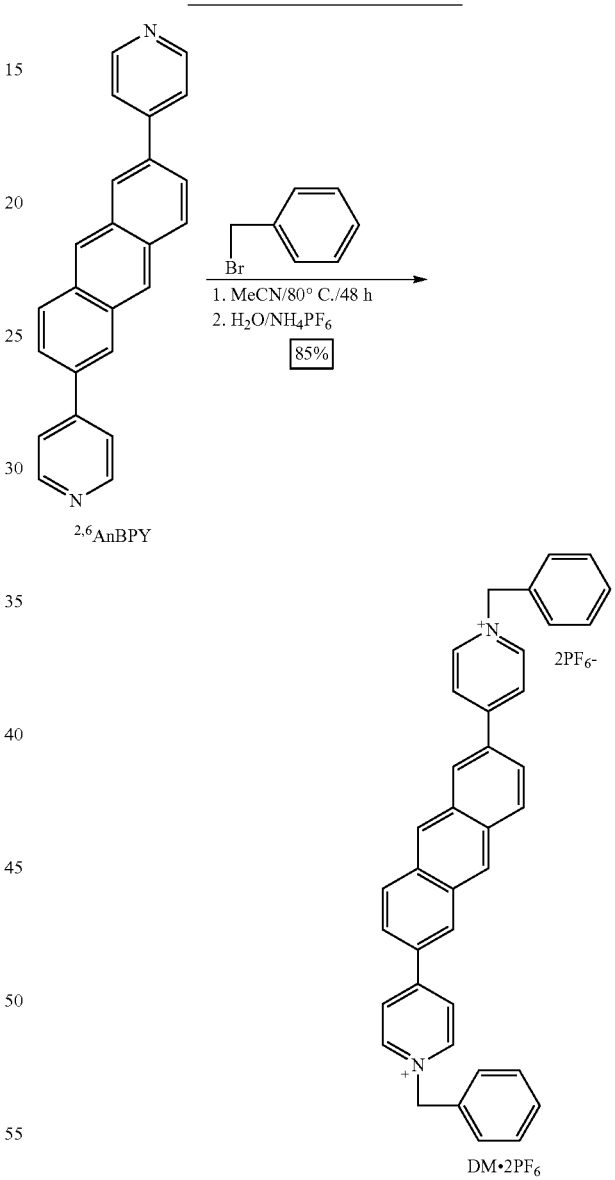

MM·PF₆: $^{2,6}$AnBPY (200 mg, 0.6 mmol) was dissolved in a dry solvent mixture (CH₂Cl₂, 10 mL: MeCN, 50 mL), in a 250-mL round-bottomed three-necked flask. The mixture was heated at 60° C. until all of the solid material dissolved. Subsequently, the temperature was raised to 90° C. prior to the addition of five aliquots of α-bromotoluene (103 mg, 0.6 mmol) in (MeCN, 10 mL), slowly during 1 h. The orange precipitate, indicative of MM·Br formation, began to appear after 30 min. The reaction mixture was heated under reflux for 48 h. After cooling to room temperature, the orange precipitate was collected by filtration and washed with CH₂Cl₂. The solid was dried in the air for 10 min and dissolved in hot MeOH (~700-900 mL). The addition of NH₄PF₆ salt (~100-200 mg) and cold (≤25° C.) H₂O (~300 mL), resulting in the precipitation of pure MM·PF₆ (272 mg, 80%) which was collected by filtration as an orange solid. ¹H NMR (500 MHz, CD₃CN, ppm): 8.83-8.75 ($H_3+H_6+H_9+H_{12}$, m, 5H), 8.74 ($H_{14}$, d, J=6.6 Hz, 4H), 8.64 ($H_5$, s, 1H), 8.44 ($H_4$, d, J=7.0 Hz, 2H), 8.34 ($H_8+H_{11}$, m, 2H), 8.12 ($H_{13}$, d, J=6.6 Hz, 4H), 7.98 ($H_7+H_{10}$, m, 2H), 7.51 ($H_1$, s, 5H), 5.73 ($H_2$, s, 2H). ¹³C NMR (125 MHz, CD₃CN, ppm): $\delta_C$=147.3, 145.3, 131.5, 131.3, 130.9, 130.8, 130.5, 130.0, 129.8, 129.4, 129.1, 126.4, 125.6, 124.5, 124.0, 64.6. (HRMS-ESI) For MM·PF₆, Calcd for $C_{31}H_{23}F_6N_2P$: m/z=423.1956 [M-PF₆]⁺; found: 423.1962 [M-PF₆]⁺.

DM·2PF₆: α-Bromotoluene (265 mg, 1.5 mmol) was dissolved in a dry solvent mixture (CH₂Cl₂, 10 mL: MeCN, 50 mL), in a 250-mL round-bottomed three-necked flask. The mixture was heated at 60° C. until all of the solid material dissolved. Subsequently, the temperature was raised to 90° C. prior to the addition of five aliquots of $^{2,6}$AnBPY (50 mg, 0.15 mmol) in (MeCN, 10 mL), slowly during 1 h. The orange precipitate, indicative of DM·2Br formation, began to appear after 30 min. The reaction mixture was heated under reflux for 48 h. After cooling to room temperature, the orange precipitate was collected by filtration and washed with $CH_2Cl_2$. The solid was dried in the air for 10 min and dissolved in hot MeOH (~700-900 mL). The addition of $NH_4PF_6$ salt (~100-200 mg) and cold (≤25° C.) $H_2O$ (~300 mL), resulting in the precipitation of pure DM·2PF$_6$ (102 mg, 85%) which was collected by filtration as an orange solid. $^1H$ NMR (500 MHz, $CD_3CN$, ppm): 8.83 ($H_5$, s, 2H), 8.80 ($H_4$, d, J=6.8 Hz, 4H), 8.78 ($H_6$, s, 2H), 8.45 ($H_3$, d, J=6.8 Hz, 4H), 8.37 ($H_8$, d, J=9.0 Hz, 2H), 8.0 ($H_7$, d, J=9.0 Hz, 2H), 7.51 ($H_1$, s, 10H), 5.74 ($H_2$, s, 4H). $^{13}C$ NMR (125 MHz, $CD_3CN$, ppm): $\delta_C$=156.83, 144.98, 133.77, 133.09, 132.97, 132.40, 131.07, 131.01, 130.46, 130.13, 129.63, 129.52, 126.13, 124.46, 64.30. (HRMS-ESI) For DM·2PF$_6$, Calcd for $C_{31}H_{23}F_6N_2P$: m/z=659.2068 [M-PF$_6$]$^+$; found: 659.2051 [M-PF$_6$]$^+$.

DFT Calculations

The structures of $^{9,10}$AnBox$^{4+}$ and $^{2,6}$AnBox$^{4+}$ and $^{2,6}$AnHC$^{8+}$ were geometry optimized at the B3LYP/6-31G level. Gas phase DFT calculation were carried at the B3LYP/6-31G+* using Jaguar software.[5] The molecular orbitals were generated with Maestro interface.

Cellular Imaging

Cell Culture and Treatment

Figure 11:
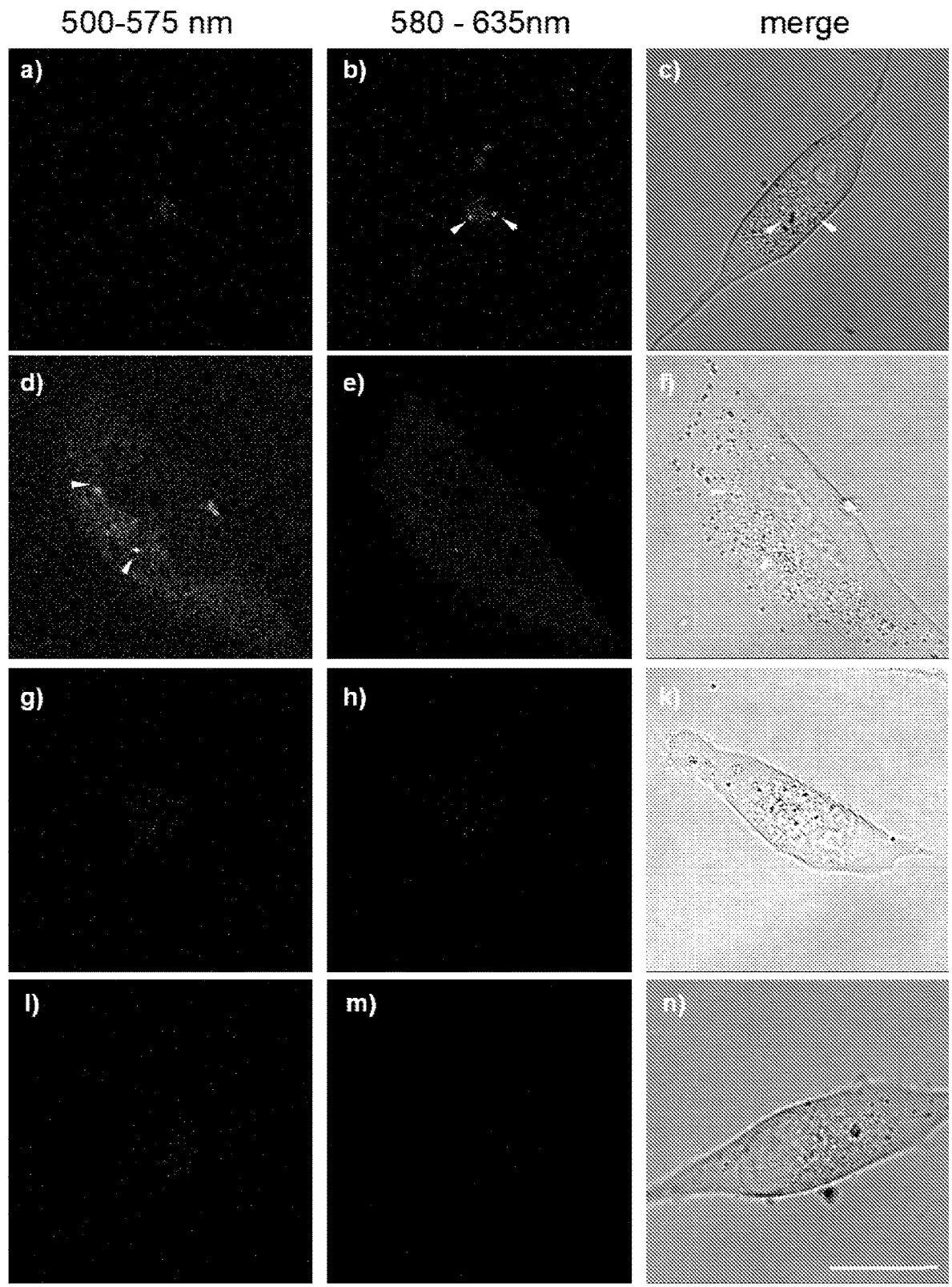
FIG. 11 shows live-cell confocal microscopy images of MIA PaCa-2 prostate cancer cells. Cells were incubated with (panels a, b, c)$^{2,6}AnHC^{8+}\cdot 8Cl$ (2.5 μM in PBS solution), (panels d, e, f)$^{2,6}AnBox^{4+}\cdot 4Cl$ (20 μM in PBS solution) and (panels g, h, k)$^{2,6}AnBox^{4+}\cdot 4Cl$ (10 μM in PBS solution). (panels 1, m, n) Vehicle control. Composed images of the cells with (panels a, d, g, 1) green emission (500-575 nm, shown in green) and (panels b, e, h, m) red emission (580-635 nm). (panels c, f, k, n) Merged images showing both emission ranges and the transmitted light images.
Figure 12:
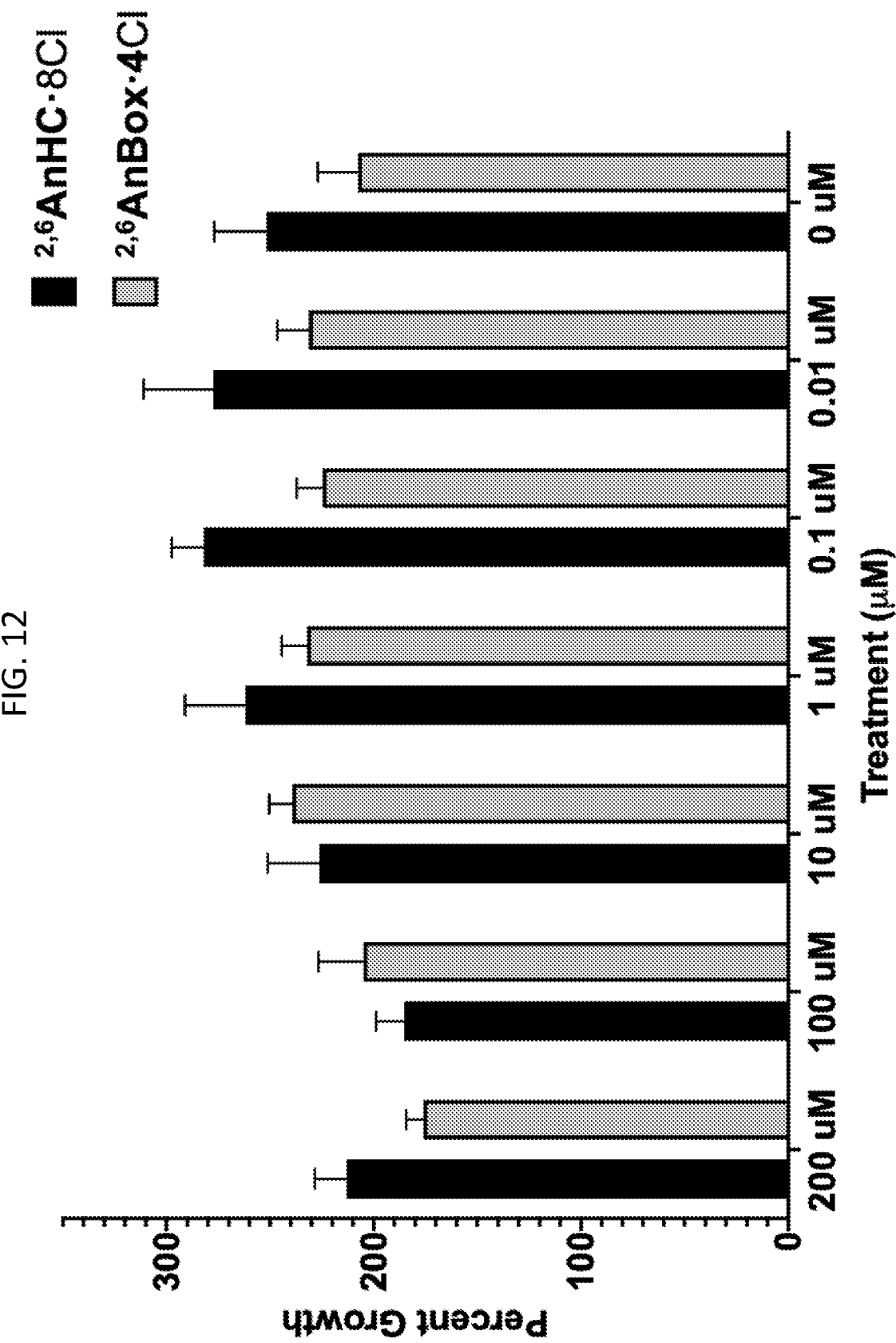
FIG. 12 shows MIA PACA2 prostate cancer cells were plated in a 96 well culture plate at a density of $0.01\times10^6$ cells per well in DMEM media (Invitrogen) with 10% FBS and 1% penicillin-streptomycin. Cells were cultured for 4 hours then treated with the compounds at a range of concentrations. Upon treatment, cells were placed in a BioTek LionheartFX system, where they were imaged every 20 minutes for 48 hours, under standard culture conditions (37° C., 5% $CO_2$). Phase contrast images were processed and analyzed with BioTek Gen5 analysis software to identify cell number at the start and end of the culture time. There was no significant difference in percent growth either between the two compounds or between the different concentrations and the untreated (0 mM) control.

Cells were grown in standard DMEM (supplemented with 10% Fetal Bovine Serum and 1% Penicillin-Streptomycin, supplier=Corning). Cells were seeded into imaging coverglass chamber 40 hours prior to treatment. Compounds were resuspended in deionized $H_2O$ then diluted to the final concentration in media. Cells were treated with compounds for 6 hours prior to imaging. Neither the catenane ($^{2,6}$AnHC.8Cl) nor the cyclophane ($^{2,6}$AnBox•4Cl) are toxic to the cells at any concentration tested (FIG. 11).

Imaging and Image Processing

All imaging was done on a Leica SP5 laser scanning confocal with LAS AF software in the Biological Imaging Facility at Northwestern University (Evanston, IL). A single excitation wavelength (458 nm) was used at a power of 5 uW. For the emission collection, two Leica spectral Hybrid (HyD) detectors were used; one was set to collect a wavelength range of 500-575 nm (with a gain of 200%) and the second was set to collect a wavelength range of 580-635 nm (with a gain of 103%). Images were processed with FIJI/ImageJ (NIH) and settings were kept consistent throughout the series of images.

REFERENCES

1. Fudickar, W.; Linker, T., Synthesis of Pyridylanthracenes and their Reversible Reaction with Singlet Oxygen to Endoperoxides. *J. Org. Chem.*, 2017, 82, 9258-9262.
2. Liu, J.; Zhu, W.; Zhou, K.; Wang, Z.; Zou, Y.; Meng, Q.; Li, J.; Zhen, Y.; Hu, W., Pyridyl-Substituted Anthracene Derivatives with Solid-State Emission and Charge Transport Properties. *J. Mater. Chem. C*, 2016, 4, 3621-3627.
3. Kodaimati, M. S.; Lian, S. C.; Schatz, G. C.; Weiss, E. A., Energy Transfer-Enhanced Photocatalytic Reduction of Protons within Quantum Dot Light-Harvesting-Catalyst Assemblies. *Proc. Natl. Acad. Sci.* USA 2018, 115, 8290-8295.
4. Thordarson, P. Determining Association Constants from Titration Experiments in Supramolecular Chemistry. *Chem. Soc. Rev.*, 2011, 40, 1305-1323.
5. Dolomanov, O. V.; Bourhis, L. J.; Gildea, R. J; Howard, J. A. K.; Puschmann, H., A Complete Structure Solution, Refinement and Analysis Program. *J. Appl. Cryst.* 2009, 42, 339-341.
6. Sheldrick, G. M. SHELXT Integrated Space-Group and Crystal-Structure Determination. *Acta Cryst.* 2015, A71, 3-8.
7. Sheldrick, G. M. A Short History of SHELX. *Acta Cryst.* 2008. A64, 112-122.
8. (a) *Jaguar*, version 9.8; Schrodinger Inc.: New York, 2017. (b) A. D. Bochevarov, E. Harder, T. F. Hughes, J. R. Greenwood, D. A. Braden, D. M. Philipp, D. Rinaldo, M. D. Halls, J. Zhang, R. A. Friesner, "Jaguar: A High-Performance Quantum Chemistry Software Program with Strengths in Life and Materials Sciences", *Int. J. Quantum Chem.*, 2013, 113, 2110-2142.

TABLES

TABLE 1

Spectroscopic Parameters of the AnDB$^{2+}$ Derivatives, $^{9,10}$AnBox$^{4+}$ and $^{2,6}$AnBox$^{4+}$ Cyclophanes and $^{2,6}$AnHC$^{8+}$ Homo [2] Catenane.

| Compound [a] | $\lambda_{abs}$ (nm) | $\lambda_{em}$ (nm) | $\tau$ (ns) | $\Phi$ (%) |
|---|---|---|---|---|
| $^{2,6}$AnDB$^{2+}$ | 453 | 542 | 10 | 7.0 |
| $^{2,6}$AnBox$^{4+}$ | 458 | 562 | 3 | 3.6 |
| $^{9,10}$AnBox$^{4+}$ | 415 | 566 | 8.7 | 1.3 |
| $^{2,6}$AnHC$^{8+}$ | 466 | 650 | 14 | 0.5 |

[a] The solutions were prepared at a concentration of $4 \times 10^{-7}$ M

TABLE 2

Summary of the Solvatochromic Effect Spectroscopic Parameters of $^{9,10}$AnBox$^{4+}$, $^{2,6}$AnBox$^{4+}$ Cyclophanes and $^{2,6}$AnHC$^{8+}$ Homo [2] Catenane.

| Compound [a] | Solvents | $\lambda_{abs}$ (nm) | $\lambda_{exc}$ (nm) | $\lambda_{em}$ (nm) | Stokes shifts ($\delta$) (cm$^{-1}$) |
|---|---|---|---|---|---|
| $^{2,6}$AnBox$^{4+}$ | Me$_2$SO | 460 | 466 | 570 | 3915 |
| | H$_2$O | 458 | 468 | 553 | 3284 |
| | DMF | 472 | 468 | 549 | 3153 |
| | MeOH | 460 | 466 | 568 | 3854 |
| | EtOH | 468 | 468 | 562 | 3574 |
| | MeCN | 458 | 460 | 562 | 3946 |
| $^{9,10}$AnBox$^{4+}$ | Me$_2$SO | 403 | 408 | 570 | 6966 |
| | H$_2$O | 419 | 419 | 566 | 6199 |
| | DMF | 402 | 414 | 576 | 6793 |
| | MeOH | 402 | 417 | 565 | 6282 |
| | EtOH | 409 | 418 | 574 | 6502 |
| | MeCN | 410 | 416 | 566 | 6371 |
| $^{2,6}$AnHC$^{8+}$ | Me$_2$SO | 456 | 453 | 595 | 5268 |
| | H$_2$O | 464 | 460 | 675 | 6924 |
| | DMF | 470 | 454 | 576 | 4665 |
| | MeOH | 470 | 456 | 606 | 5428 |
| | EtOH | 460 | 458 | 610 | 5441 |
| | MeCN | 472 | 460 | 652 | 6402 |

[a] The solutions were prepared at a concentration of $4 \times 10^{-7}$ M

We claim:

1. A method for live-cell imaging, the method comprising:
    (a) contacting a cell with an effective amount of a catenane;
    (b) irradiating the cell;
    (c) detecting exciplex emission from the catenane within the cell,
    wherein the catenane comprises two mechanically interlocked macrocycles, each of the two macrocycles comprise an aromatic fluorophore subunit, and
    wherein the aromatic fluorophores are arranged in a face-to-face [π . . . π] stack allowing for the exciplex emission.

2. The method of claim 1, wherein the aromatic fluorophore comprises an anthracene subunit.

3. The method of claim 2, wherein the aromatic fluorophore comprises an anthracene-bypyridine subunit.

4. The method of claim 3, wherein the anthracene-bypyridine subunit is a 2,6-anthracene-bypyridine subunits.

5. The method of claim 1, wherein the effective amount of the catenane is less than $10 \times 10^{-6}$ M.

6. The method of claim 1, wherein the detected emission has a wavelength greater than 600 nm.

7. The method of claim 1, wherein the cell is irradiated with a wavelength less than 500 nm.

8. The method of claim 1, wherein the catenane is octacationic.

9. The method of claim 1, wherein each of the two macrocycles comprise two aromatic fluorophore subunits and the four aromatic fluorophore subunits are arranged in a face-to-face [π . . . π] stack.

10. The method of claim 1, wherein the method is performed in vitro.

11. The method of claim 1, wherein the catenane is $^{2,6}\text{AnHC}^{8+}$.

* * * * *